(12) United States Patent
Bozik et al.

(10) Patent No.: US 8,017,598 B2
(45) Date of Patent: Sep. 13, 2011

(54) COMPOSITIONS OF R(+) AND S(−) PRAMIPEXOLE AND METHODS OF USING THE SAME

(75) Inventors: Michael E. Bozik, Pittsburgh, PA (US); Thomas Petzinger, Jr., Pittsburgh, PA (US); Valentin Gribkoff, Wallingford, CT (US)

(73) Assignee: Knopp Neurosciences, Inc., Pittsburgh, PA (US)

( * ) Notice: Subject to any disclaimer, the term of this patent is extended or adjusted under 35 U.S.C. 154(b) by 0 days.

(21) Appl. No.: 11/749,497

(22) Filed: May 16, 2007

(65) Prior Publication Data

US 2008/0014259 A1    Jan. 17, 2008

Related U.S. Application Data

(63) Continuation-in-part of application No. 11/733,642, filed on Apr. 10, 2007, now abandoned.

(60) Provisional application No. 60/747,320, filed on May 16, 2006, provisional application No. 60/870,009, filed on Dec. 14, 2006, provisional application No. 60/894,799, filed on Mar. 14, 2007, provisional application No. 60/894,829, filed on Mar. 14, 2004, provisional application No. 60/894,835, filed on Mar. 14, 2007.

(51) Int. Cl.
*A01N 43/00* (2006.01)
*A01N 43/78* (2006.01)
*A61K 31/33* (2006.01)
*A61K 31/425* (2006.01)

(52) U.S. Cl. ........................ 514/183; 514/367
(58) Field of Classification Search .................. 514/183, 514/367
See application file for complete search history.

(56) References Cited

U.S. PATENT DOCUMENTS

| | | |
|---|---|---|
| 3,598,122 A | 8/1971 | Zaffaroni |
| 3,598,123 A | 8/1971 | Zaffaroni |
| 3,731,683 A | 5/1973 | Zaffaroni |
| 3,797,494 A | 3/1974 | Zaffaroni |
| 4,031,894 A | 6/1977 | Urquhart et al. |
| 4,144,317 A | 3/1979 | Higuchi et al. |
| 4,201,211 A | 5/1980 | Chandrasekaran et al. |
| 4,286,592 A | 9/1981 | Chandrasekaran et al. |
| 4,314,557 A | 2/1982 | Chandrasekaran et al. |
| 4,327,725 A | 5/1982 | Cortese et al. |
| 4,379,454 A | 4/1983 | Campbell et al. |
| 4,395,859 A | 8/1983 | Rohrer |
| 4,435,180 A | 3/1984 | Leeper |
| 4,559,222 A | 12/1985 | Enscore et al. |
| 4,568,343 A | 2/1986 | Leeper et al. |
| 4,573,995 A | 3/1986 | Chen et al. |
| 4,588,580 A | 5/1986 | Gale et al. |
| 4,612,008 A | 9/1986 | Wong et al. |
| 4,626,539 A | 12/1986 | Aungst et al. |
| 4,645,502 A | 2/1987 | Gale et al. |
| 4,698,062 A | 10/1987 | Gale et al. |
| 4,704,282 A | 11/1987 | Campbell et al. |
| 4,725,272 A | 2/1988 | Gale |
| 4,731,374 A | 3/1988 | Griss et al. |
| 4,781,924 A | 11/1988 | Lee et al. |
| 4,783,337 A | 11/1988 | Wong et al. |
| 4,788,062 A | 11/1988 | Gale et al. |
| 4,806,341 A | 2/1989 | Chien et al. |
| 4,816,258 A | 3/1989 | Nedberge et al. |
| 4,843,086 A | 6/1989 | Griss et al. |
| 4,849,226 A | 7/1989 | Gale |
| 4,886,812 A * | 12/1989 | Griss et al. .................... 514/321 |
| 4,904,475 A | 2/1990 | Gale et al. |
| 4,908,027 A | 3/1990 | Enscore et al. |
| 4,917,895 A | 4/1990 | Lee et al. |
| 4,938,759 A | 7/1990 | Enscore et al. |
| 4,943,435 A | 7/1990 | Baker et al. |
| 5,004,610 A | 4/1991 | Osborne et al. |
| 5,024,843 A | 6/1991 | Kuczynski et al. |
| 5,069,909 A | 12/1991 | Sharma et al. |
| 5,071,656 A | 12/1991 | Lee et al. |
| 5,082,668 A | 1/1992 | Wong et al. |
| 5,091,190 A | 2/1992 | Kuczynski et al. |
| 5,112,842 A | 5/1992 | Zierenberg et al. |
| 5,122,382 A | 6/1992 | Gale et al. |
| 5,141,750 A | 8/1992 | Lee et al. |
| 5,284,660 A | 2/1994 | Lee et al. |
| 5,314,694 A | 5/1994 | Gale et al. |
| 5,342,623 A | 8/1994 | Enscore et al. |
| 5,411,740 A | 5/1995 | Lee et al. |
| 5,442,117 A | 8/1995 | Stahly et al. |
| 5,545,413 A | 8/1996 | Kuczynski et al. |
| 5,591,454 A | 1/1997 | Kuczynski et al. |
| 5,635,203 A | 6/1997 | Gale et al. |
| 5,650,420 A | 7/1997 | Hall et al. |

(Continued)

FOREIGN PATENT DOCUMENTS

AU    2006279643 B2    8/2006

(Continued)

OTHER PUBLICATIONS

Biglan (Expert Opinion on Pharmacotherapy (2002) 3:197-210).*
Berge et al., Pharmaceutical Salts, 1977, J. Pharm. Sciences 66(1):1-19.
Banker et al., Modern Pharmaceutics, Marcel Dekker, Inc. 1979 (TOC).
Goodman et al., The Pharmaceutical Basis of Therapeutics, 6$^{th}$ Ed., MacMillan Publishing Co., New York, 1980 (TOC).
Petersen et al., Impaired Mitochondrial Activity in the Insulin-Resistant Offspring of Patients with Type 2 Diabetes, 2004, New England Journal of Medicine 350:664-671.

(Continued)

*Primary Examiner* — Marcos L Sznaidman
(74) *Attorney, Agent, or Firm* — Pepper Hamilton LLP

(57) ABSTRACT

Compositions of predetermined amounts of R(+) pramipexole and S(−) pramipexole and methods of using the same, including for the treatment and prevention of Parkinson's disease, are provided.

42 Claims, No Drawings

U.S. PATENT DOCUMENTS

| | | | |
|---|---|---|---|
| 5,674,895 | A | 10/1997 | Guittard et al. |
| 5,804,215 | A | 9/1998 | Cubbage et al. |
| 5,830,497 | A | 11/1998 | Yamanaka et al. |
| 5,840,754 | A | 11/1998 | Guittard et al. |
| 5,912,268 | A | 6/1999 | Guittard et al. |
| 6,156,777 | A | 12/2000 | Hall et al. |
| 6,187,802 | B1 | 2/2001 | Cheetham et al. |
| 6,262,115 | B1 | 7/2001 | Guittard et al. |
| 6,443,976 | B1 | 9/2002 | Flower et al. |
| 6,480,820 | B1 | 11/2002 | Clopton et al. |
| 6,541,486 | B1 | 4/2003 | Bitler et al. |
| 6,727,367 | B2 | 4/2004 | Pospisilik |
| 6,750,235 | B1 | 6/2004 | Rosenbaum |
| 6,919,092 | B2 | 7/2005 | Guittard et al. |
| 6,919,373 | B1 | 7/2005 | Lam et al. |
| 6,929,801 | B2 | 8/2005 | Klose et al. |
| 6,930,129 | B2 | 8/2005 | Lam et al. |
| 2002/0103240 | A1 | 8/2002 | Pospisilik |
| 2002/0106731 | A1 | 8/2002 | Ruben et al. |
| 2002/0177626 | A1 | 11/2002 | Cook et al. |
| 2003/0049318 | A1 | 3/2003 | Davis et al. |
| 2003/0203055 | A1 | 10/2003 | Rao et al. |
| 2004/0097540 | A1 | 5/2004 | Peters et al. |
| 2004/0122104 | A1 | 6/2004 | Hirsh et al. |
| 2004/0132826 | A1 | 7/2004 | Hirsh et al. |
| 2004/0219213 | A1 | 11/2004 | Burnside et al. |
| 2004/0265370 | A1 | 12/2004 | Odidi et al. |
| 2005/0031667 | A1 | 2/2005 | Patel et al. |
| 2005/0032856 | A1 | 2/2005 | Bennett, Jr. |
| 2005/0053649 | A1 | 3/2005 | Chalmers |
| 2005/0059717 | A1 | 3/2005 | Van Eupen et al. |
| 2005/0074865 | A1 | 4/2005 | Afeyan et al. |
| 2005/0089575 | A1 | 4/2005 | Friedl et al. |
| 2005/0220877 | A1 | 10/2005 | Patel et al. |
| 2005/0226926 | A1 | 10/2005 | Amidon et al. |
| 2005/0265379 | A1 | 12/2005 | Rao |
| 2006/0051419 | A1 | 3/2006 | Friedl et al. |
| 2006/0069263 | A1 | 3/2006 | Gribun et al. |
| 2006/0099257 | A1 | 5/2006 | Langridge et al. |
| 2006/0106224 | A1 | 5/2006 | Gupta et al. |
| 2006/0110450 | A1 | 5/2006 | Eisenreich |
| 2006/0141037 | A1 | 6/2006 | Mehta et al. |
| 2006/0148866 | A1 | 7/2006 | Xia et al. |
| 2006/0281797 | A1 | 12/2006 | Bennett, Jr. |
| 2006/0286167 | A1 | 12/2006 | Staunton et al. |
| 2007/0105918 | A1 | 5/2007 | Bennett, Jr. |
| 2007/0203209 | A1 | 8/2007 | Bartolini et al. |
| 2007/0259930 | A1 | 11/2007 | Bozik et al. |
| 2008/0014259 | A1 | 1/2008 | Bozik et al. |
| 2008/0020028 | A1 | 1/2008 | Shevchuk et al. |
| 2008/0026043 | A1 | 1/2008 | Mueller et al. |
| 2008/0081041 | A1 | 4/2008 | Nemeth |
| 2008/0096939 | A1 | 4/2008 | Keil et al. |
| 2008/0227985 | A1 | 9/2008 | Raje et al. |
| 2009/0042956 | A1 | 2/2009 | Bozik et al. |
| 2009/0054504 | A1 | 2/2009 | Bozik et al. |
| 2009/0149518 | A1 | 6/2009 | Nishii et al. |

FOREIGN PATENT DOCUMENTS

| | | | |
|---|---|---|---|
| EP | 0186087 A1 | 7/1986 | |
| EP | 2156833 A1 | 2/2010 | |
| JP | 2009-504748 A | 2/2009 | |
| WO | WO 1993/17683 A1 | 9/1993 | |
| WO | WO 03/049705 A2 | 6/2003 | |
| WO | WO 2003/049705 | * | 6/2003 |
| WO | WO 2004/041797 A1 | 5/2004 | |
| WO | WO 2005/011687 A1 | 2/2005 | |
| WO | WO 2006/003471 A2 | 1/2006 | |
| WO | WO 2006/012277 A | 2/2006 | |
| WO | WO 2006/015944 A2 | 2/2006 | |
| WO | WO 2007/022182 A1 | 2/2007 | |
| WO | WO 2007/045620 A | 4/2007 | |
| WO | WO 2007/075095 A1 | 7/2007 | |
| WO | WO 2007/090882 A2 | 8/2007 | |
| WO | WO 2007/121188 A | 10/2007 | |
| WO | WO 2007/137071 A2 | 11/2007 | |
| WO | WO 2008/023027 A2 | 2/2008 | |
| WO | WO 2008/041240 A2 | 4/2008 | |
| WO | 2008/074033 | 6/2008 | |
| WO | 2008/113003 | 9/2008 | |
| WO | WO 2008/104847 A2 | 9/2008 | |
| WO | WO 2008/113003 A1 | 9/2008 | |
| WO | WO 2008/113056 A2 | 9/2008 | |
| WO | WO 2010/022140 A1 | 2/2010 | |

OTHER PUBLICATIONS

Cassarino et al., An evaluation of the role of mitochondria in neurodegenerative diseases: mitochondrial mutations and oxidative pathology, protective nuclear responses, and cell death in neurodegeneration, 1999, Brain Res. Rev. 29:1-25.

Danseizen et al., Targeted Antioxidative and Neuroprotective Properties of the Dopamine Agonist Pramipexole and Its Nondopaminergic Enantiomer SND919CL2x [(+)2-Amino-4, 5, 6, 7-tetrahydro-6-L-propylamino-benzathiazole Dihydrochloride], 2006, J. Pharmacol. Exp. Ther. 316:189-199.

Remington, The Science and Practice of Pharmacy, $20^{th}$ ed., Lippincott Williams & Wilkins, Baltimore, MD, Ch. 38:704-720.

Jacques et al., Enantiomers, Racemates and Resolutions, John Wiley and Sons, Inc., Canada, 1981 (TOC).

Mierau et al., Pramipexole binding and activation of cloned and expressed dopamine $D_2$, $D_3$ and $D_4$ receptors, 1995, Eur. J. Pharmacol. 290:29-36.

Gu et al., Pramipexole protects against apoptotic cell death by non-dopaminergic mechanisms, 2004, J. Neurochem. 91:1075-1081.

Lieberman et al., Pharmaceutical Dosage Forms: Tablets, New York: Marcel Dekker, Inc. 1989 (TOC).

Ansel et al., Pharmaceutical Dosage Forms and Drug Delivery Systems, $6^{th}$ ed., Media, PA, Williams & Wilkins, 1995 (TOC).

Abramova et al. "Inhibition by R(+) or S(−) Pramipexole of Caspase Activation and Cell Death Induced by Methylpyridinium Ion or Beta Amyloid Peptide in SH-SY5Y Neuroblastoma" 2002, *J. Neurosc. Res.* 67(4):494-500. XP009075274.

Anasova et al. "Antigenecity and Immunogenicity of Allogeneic Retinal Transplants" Oct. 2001, *J. Clin. Invest.* 108(8):1175-1183.

Anonymous "Variant of Parkinson's Drug Tested in ALS" Jul. 19, 2006 (printed from www.als-mda.org/research/news/060719als pramipexole.html on Feb. 21, 2008) (Abstract). XP002469993.

Ashcroft et al. "An Efficient and Scalable Synthesis of the Endothelin Antagonists UK-350,926 and UK-349,862 Using a Dynamic Resolution Process" 2005, *Organic Proc. Res. & Dev.* 9:663-669.

Balicki et al. "A New, Efficient and Economic Method for Preparation of Pramipexole" May 16, 2006, Book of Abstracts: The Fifth Multidisciplinary conference on Drug Research, *Pielaszek Research* (Warszawa, Poland) Poster No. 1-19, p. 30 (English Abstract).

Balicki et al. "New method for preparing pramipexole dihydrochloride monohydrate" 2006, *Przemysl Chemiczny* 85(5):344-346.

Beatty et al. "The Role of Oxidative Stress in the Pathogenesis of Age-Related Macular Degeneration" 2000, *Surv. Opthalmol* 45(2):115-134.

Feher et al. "Mitochondrial alternations of retinal pigment epithelium in age-related macular degenteration" Jun. 2006 (Printed from http://www.neurobiologyofaging.org/article/PIISO1974580005001545 on Dec. 11, 2009) *Neurobiology of Aging* 27(7) (Abstract, 2 pages).

Golebiewski et al. "Application of GC/MS for Identyification of the Sideproducts in a Process of Preparation of Pramipexole" May 16, 2006, Book of Abstracts: The Fifth Multidisciplinary conference on Drug Research, *Pielaszek Research* (Warszawa, Poland) Poster No. 1-57, p. 49.

Hansen et al. "First Generation Process for the Preparation of the DPP-IV Inhibitor Sitagliptin" 2005, *Organic Proc. Res. & Dev.* 9:634-639.

Hasegawa et al. "A New Process for Synthesis of the Astrocyte Activation Suppressor, ONO-2506" 2005, *Organic Proc. Res. & Dev.* 9:774-781.

Initial Scientific Discussion for the Approval of Mirapex from the European Agency for the Evaluation of Medicinal Products (EMEA) www.emea.europa.eu/humandocs/PDFS/EPAR/Mirapexin/059097en6.pdf.

Liang et al. "Oxidative stress-induced mitochondrial DNA damage in human retinal pigment epithelial cells: a possible mechanism for RPE aging and age-related macular degeneration" 2003, *Exp. Eye Res.* 76(4):397-403.

Matthews et al. "Assessment of the Health Effects of Chemicals in Humans: I. Qsar Estimation of the Maximum Recommended Therapeutic Dose (MRTD) and No Effect Level (NOEL) of Organic Chemicals Based on Clinical Trial Data" 2004, *Current Drug Discovery Technologies* 1:61-76.

Public Statement on Mirapex, Sudden Onset of Sleep from the European Agency for the Evaluation of Medicinal Products (EMEA) www.emea.europa.eu/pdfs/human/press/pus/2064299.pdf.

Roca-Santiago et al. "Alzheimer's Disease and Age-related Macular Degeneration" Feb. 2006, *Arch. Soc. Esp. Oftalmol.* 81 (2):73-78.

Schmidt et al. "Neurodegenerative diseases of the retina and potential for protection and recovery" Jun. 2008 (printed from http://www.nncbi.nim,nih.gov/pubmed/19305795?dopt_Abstract) *Curr. Neuropharmacol.* 6(2) (Abstract, 1 page).

Schneider et al. "Dopamine Autoreceptor Agonists: Resolution and Pharmacological Activity of 2,6-Diaminotetrahydrobenzothiazole and an Aminothiazole Analogue of Apomorphine" 1987, *J. Med. Chem.* 30:494-498.

Schuelke et al. "Myostatin Mutation Associated With Gross Muscle Hypertrophy in a Child" 2004, *N. Engl. J. Med.* 350:2682-2688 (Para.1).

The Foundation Fighting Blindness "Animal Models for Studying Inherited Degenerative Retinal Disease" 2000 (printed from www.retina-international.org/sci-news/animmod.doc on Jan. 11, 2009) *The Foundation Fighting Blindness* (23 pages).

Tobran-Tink et al. "Neuroprotection in Macular Degeneration" 2005, *Age-Related Macular Degeneration: A Comprehensive Textbook* (Lippincott Williams & Wilkins), 29:335-336.

Wong et al. "Activation of Extracellular Signal-Regulated Kinase by Dopamine D2 and D3 Receptors" 2003, *Society for Neuroscience Abstracts* (retrieved on line at sfn.scholarone.com/itin2003/main.html?new_page_id=126&abstract_id=3866&p_num=363.4&is_tech=0 on Jun. 23, 2008).

Agardh et al. "Expression of antioxidant enzymes in rat retinal ischemia followed by reperfusion" Jul. 2006, *Metabolism* 55(7):892-898 (Abstract).

Halestrap "The Role of Mitochondria in Cell Death" Mar. 24, 2003, *Endocrine Abstracts* 5:513 (Abstract).

Love "Oxidative Stress in Brain Ischemia" Apr. 5, 1999, *Brain Pathology* 9(1)119-131 (Abstract).

Winkler et al. "Oxidative damage and age-related macular degeneration" Nov. 3, 1999, *Mol. Vis.* 5:32 (Abstract).

Cassarino et al. "Pramipexole reduces reactive oxygen species production in vivo and in vitro and inhibits the mitochondrial permeability transition produced by the parkinsonian neurotoxin methylpyridinium ion" 1998, *J. Neurochem.* 71(1):295-301.

Corrigan et al. "Comparison of Pramipexole, Fluoxetine, and Placebo in Patients with Major Depression" 2000, *Depression and Anxiety* 11:58-65.

European Supplemental Search Report dated Apr. 8, 2010 for EP 08743922 (903).

European Supplemental Search Report dated Apr. 9, 2010 for EP 08732306.9 (503).

European Supplemental Search Report dated Nov. 23, 2006 for EP02795869.

International Search Report and Written Opinion dated Aug. 25, 2010 for PCT/US2010/39379 (1302).

International Search Report and Written Opinion dated Jun. 29, 2009 for PCT/US2008/057158 (502).

International Search Report dated Apr. 4, 2008 for PCT/US2007/087639 (702).

International Search Report dated Jul. 11, 2008 for PCT/US2008/057059 (902).

International Search Report dated Jul. 17, 2003 for PCT/US2002/39970.

International Search Report dated Oct. 22, 2009 for PCT/US2009/54292.

Kieburtz "Safety and Efficacy of Pramipexole in Early Parkinson Disease" 1997, *JAMA* 278(2):125-130.

Lieberman et al. "Clinical evaluation of pramipexole in advanced Parkinson's disease: Results of a double-blind, placebo-controlled, parallel-group study" 1997, *Neurology* 49:162-168.

Pattee et al. "Reduction of oxidative stress in amyotrophic lateral sclerosis following pramipexole treatment" Jan. 2003, *Amyotrophic Lateral Sclerosis and Other Motor Neuron Disorders* 4(2):90-95 (abstract).

Schilling et al. "Neuroendocrine and side effect profile of pramipexole, a new dopamine receptor agonist, in humans" 1992, *Clin. Pharmacol. Ther.* 51:541-548.

Shannon et al. "Efficacy of Pramipexole, a Novel Dopamine Agonist, as Monotherapy in Mild to Moderate Parkinson's Disease" 1997, *Neurology* 49(3)a;724-728.

Wong "A 384-well cell-based phosphor-ERK assay for dopamine D2 and D3 receptors" 2004, *Analytical Biochem.* 333:265-272.

Worker "Novel Therapeutic Strategies" 1999, IDRUGS, *Current Drugs Ltd.* GB 2(9):848-852 (XP000972503).

Wright et al. "Influence of Probenecid (PR) and Cimetidine (C) on Pramipexole (PX) Pharmacokinetics" Feb. 1995, *Clin. Pharmacol. & Ther.* 59(2):PII-99 (abstract).

\* cited by examiner

COMPOSITIONS OF R(+) AND S(−) PRAMIPEXOLE AND METHODS OF USING THE SAME

CROSS-REFERENCE TO RELATED APPLICATIONS

This application claims the benefit of U.S. Provisional Application Ser. No. 60/747,320 entitled "Tetrahydrobenzothiazoles and Uses Thereof" filed May 16, 2006; U.S. Provisional Application Ser. No. 60/870,009 entitled "Compositions and Methods of Using R(+) Pramipexole", filed Dec. 14, 2006; U.S. Provisional Application Ser. No. 60/894,799 entitled "Modified Release Formulations and Methods of Use of R(+) Pramipexole" filed Mar. 14, 2007; U.S. Provisional Application Ser. No. 60/894,829 entitled "Methods of Synthesizing and Purifying R(+) and S(−) Pramipexole" filed Mar. 14, 2007; and U.S. Provisional Application Ser. No. 60/894,835 entitled "Compositions and Methods of Using R(+) Pramipexole" filed Mar. 14, 2007; each of which is incorporated herein by reference in their entireties. Further, this application is a continuation-in-part of and claims priority to U.S. Application Ser. No. 11/733,642 entitled "Compositions and Methods of Using R(+) Pramipexole" filed Apr. 10, 2007, which is incorporated herein by reference in its entirety.

GOVERNMENT INTERESTS

Not applicable

PARTIES TO A JOINT RESEARCH AGREEMENT

Not applicable

INCORPORATION BY REFERENCE OF MATERIAL SUBMITTED ON A COMPACT DISC

Not applicable

BACKGROUND

1. Field of Invention
Not applicable
2. Description of Related Art
Not applicable

G. BRIEF SUMMARY OF THE INVENTION

Embodiments of the present invention related to multicomponent pharmaceutical compositions comprising a first component and a second component, wherein said first component comprises R(+) pramipexole and said second component comprises S(−) pramipexole. Such multicomponent pharmaceutical compositions may comprise immediate release formulations, sustained release formulations or a combination thereof. Preferably, the multicomponent pharmaceutical compositions comprises a therapeutically effective amount of R(+) pramipexole and a therapeutically effective amount of S(−) pramipexole. In further embodiments, each component may have a chiral purity for the respective enantiomer of 80% or greater, 90% or greater, 95% or greater, preferably 99% or greater, and more preferably 100%.

Further embodiments of the present invention related to sustained release pharmaceutical compositions comprising S(−) pramipexole and R(+) pramipexole in a sustained release matrix. In certain embodiments, the R(+) pramipexole may be in a first sustained release matrix and the S(−) pramipexole may be in a second sustained release matrix. Preferably, the sustained release pharmaceutical composition comprises a therapeutically effective amount of R(+) pramipexole and a therapeutically effective amount of S(−) pramipexole. In further embodiments, the chiral purity for the respective enantiomers may be 80% or greater, 90% or greater, 95% or greater, preferably 99% or greater, and more preferably 100%.

Further embodiments related to methods of treating or preventing Parkinson's disease or the symptoms thereof comprising administering a therapeutically effective amount of R(+) pramipexole and an amount of S(−) pramipexole, including, for example, multicomponent pharmaceutical compositions and sustained release pharmaceutical compositions. In certain embodiments, the amount of S(−) pramipexole is preferably a therapeutically effective amount. In certain embodiments, the amount of S(−) pramipexole is preferably a no observable adverse effect amount.

Additional embodiments relate to methods of treating or preventing Parkinson's disease or the symptoms thereof comprising administering a therapeutically effective amount of R(+) pramipexole, preferably having a chiral purity for the R(+) pramipexole of 80% or greater, 90% or greater, 95% or greater, preferably 99% or greater, and more preferably 100%.

DESCRIPTION OF DRAWINGS

Not applicable

DETAILED DESCRIPTION

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. All publications mentioned herein are incorporated by reference in their entirety.

It must also be noted that as used herein and in the appended claims, the singular forms "a", "an", and "the" include plural reference unless the context clearly dictates otherwise. Thus, for example, reference to a "salt" is a reference to one or more organic solvents and equivalents thereof known to those skilled in the art, and so forth.

As used herein, the term "about" means plus or minus 10% of the numerical value of the number with which it is being used. Therefore, about 50% means in the range of 45%-55%. Unless defined otherwise, all technical and scientific terms used herein have the same meanings as commonly understood by one of ordinary skill in the art.

As use herein, the terms "administration of" and or "administering" a compound should be understood to mean providing a compound of the invention or a prodrug of a compound of the invention to an individual in need of treatment. Within the scope of the use according to the invention pramipexole ma be administered, for example, orally, transdermally, intrathecally, by inhalation or parenterally.

As used herein, the terms "enantiomers", "stereoisomers" and "optical isomers" may be used interchangeably, and refer to molecules which contain an asymmetric or chiral center and are mirror images of one another. Further, the terms "enantiomers", "stereoisomers" or "optical isomers" describe a molecule which, in a given configuration, cannot be superimposed on its mirror image. As used herein, the term "optically pure" or "enantiomerically pure" may be taken to indicate that the compound contains at least 99.5% of a single optical isomer. The term "enantiomerically enriched" may be taken to indicate that at least 51% of the material is a single optical isomer or enantiomer. The term "enantiomeric enrichment" as used herein refers to an increase in the amount of one enantiomer as compared to the other. A "racemic" mixture is a mixture of equal amounts of R(+) and S(−) enantiomers of a chiral molecule. Throughout this invention, the word "pramipexole" will refer to both the R(+) enantiomer and the S(−) enantiomer of pramipexole.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

"Therapeutically effective amount" as used herein refers to the amount of active compound or pharmaceutical agent that elicits a biological or medicinal response in a tissue, system, animal, individual or human that is being sought by a researcher, veterinarian, medical doctor or other clinician, which includes one or more of the following: (1) preventing the disease; for example, preventing a disease, condition or disorder in an individual that may be predisposed to the disease, condition or disorder but does not yet experience or display the pathology or symptomatology of the disease, (2) inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) ameliorating the disease; for example, ameliorating a disease, condition or disorder in an individual that is experiencing or displaying the pathology or symptomatology of the disease, condition or disorder (i.e., reversing the pathology and/or symptomatology).

The term "unit dose" as used herein may be taken to indicate a discrete amount of the therapeutic composition which comprises a predetermined amount of the active compound. The amount of the active ingredient is generally equal to the dosage of the active ingredient which may be administered once per day, or may be administered several times a day (e.g. the unit dose is a fraction of the desired daily dose). The unit dose may also be taken to indicate the total daily dose, which may be administered once per day or may be administered as a convenient fraction of such a dose (e.g. the unit dose is the total daily dose which may be given in fractional increments, such as, for example, one-half or one-third the dosage).

A "No Observable Adverse Effect Level" (NOAEL) dose as used herein refers to an amount of active compound or pharmaceutical agent that produces no statistically or biologically significant increases in the frequency or severity of adverse effects between an exposed population and its appropriate control; some effects may be produced at this level, but they are not considered as adverse, or as precursors to adverse effects. The exposed population may be a system, animal, individual or human that is being treated by a researcher, veterinarian, medical doctor or other clinician. With respect to S(−) pramipexole, exemplary adverse events are dizziness, hallucination, nausea, hypotension, somnolence, constipation, headache, tremor, back pain, postural hypotension, hypertonia, depression, abdominal pain, anxiety, dyspepsia, flatulence, diarrhea, rash, ataxia, dry mouth, extrapyramidal syndrome, leg cramps, twitching, pharyngitis, sinusitis, sweating, rhinitis, urinary tract infection, vasodilation, flu syndrome, increased saliva, tooth disease, dyspnea, increased cough, gait abnormalities, urinary frequency, vomiting, allergic reaction, hypertension, pruritis, hypokinesia, nervousness, dream abnormalities, chest pain, neck pain, paresthesia, tachycardia, vertigo, voice alteration, conjunctivitis, paralysis, tinnitus, lacrimation, mydriasis and diplopia.

For example, a dose of 1.5 mg of S(−) pramipexole has been shown to cause somnolence in human subjects (*Public Statement on Mirapex®, Sudden Onset of Sleep* from the European Agency for the Evaluation of Medicinal Products; Boehringer Ingelheim product insert for Mirapex® which indicates that the drug is administered as three doses per day). Further, studies performed in dogs, as presented herein, (see Examples and results shown in Table 4) indicate that the NOAEL dose may be as low as 0.00125 mg/kg, which is equivalent to a human dose of 0.0007 mg/kg or 0.05 mg for a 70 kg individual. Thus, with reference to S(−) pramipexole, a NOAEL dose amount may be an amount below 1.5 mg, below 0.50 mg, or more preferably below 0.05 mg.

A "maximum tolerated dose" (MTD) as used herein refers to an amount of active compound or pharmaceutical agent which elicits significant toxicity in a tissue, system, animal, individual or human that is being treated by a researcher, veterinarian, medical doctor or other clinician. Single dose toxicity of S(−) pramipexole after oral administration has been studied in rodents, dogs, monkeys and human. In rodents, deaths occurred at doses of 70-105 mg/kg and above (*Initial Scientific Discussion for the Approval of Mirapex* from the European Agency for the Evaluation of Medicinal Products). This is equivalent to a human dose of 7-12 mg/kg, or approximately 500-850 mg for a 70 kg individual. Further, the Boehringer Ingelheim product insert for Mirapex® sets the maximally tolerated dose for humans at 4.5 mg/day. In human subjects, initial, single doses greater than 0.20 milligrams were not tolerated. In dogs, vomiting occurred at 0.0007 mg/kg and above while monkeys displayed major excitation at 3.5 mg/kg. All species showed signs of toxicity related to exaggerated pharmacodynamic responses to S(−) pramipexole. For example, behavioral changes including hyperactivity were common and led to a number of secondary effects, such as reduced body weight and other stress-induced symptoms. In minipigs and monkeys, S(−) pramipexole moderately affected cardiovascular parameters. In rats, the potent prolactin-inhibitory effect of pramipexole affected reproductive organs (e.g. enlarged corpora lutea, pyometra), and showed a dose-related retinal degeneration during long-term exposure (*Initial Scientific Discussion for the Approval of Mirapex* from the European Agency for the Evaluation of Medicinal Products).

Studies in dogs disclosed herein (see Examples and results in Table 3) indicate that the MTD may be as low as 0.0075 mg/kg, which is equivalent to a human dose of 0.0042 mg/kg or 0.30 mg for a 70 kg individual. Thus, with reference to S(−) pramipexole, a MTD amount for a human subject may be an amount below 4.5 mg/day, preferably below 1.5 mg/day. Further, the MTD amount for a human subject may be an amount below 0.3 mg/dose based on results of studies disclosed herein (see Table 3), and preferably below 0.2 mg/dose.

The term "treating" may be taken to mean prophylaxis of a specific disorder, disease or condition, alleviation of the symptoms associated with a specific disorder, disease or condition and/or prevention of the symptoms associated with a specific disorder, disease or condition.

The term "patient" and "subject" are interchangeable and may be taken to mean any living organism which may be treated with compounds of the present invention. As such, the terms "patient" and "subject" may include, but is not limited to, any non-human mammal, primate or human.

Although any methods and materials similar or equivalent to those described herein can be used in the practice or testing of embodiments of the present invention, the preferred methods, devices, and materials are now described.

The compound 2-amino-4,5,6,7-tetrahydro-6-(propylamino)benzothiazole is a synthetic aminobenzothiazole derivative. The S(−) enantiomer, commonly known simply as pramipexole, is a potent agonist at the D2 family of dopamine receptors, with predominant affinity for the $D_3$ receptor subtype. As a dopamine agonist, S(−) pramipexole activates dopamine receptors, thus mimicking the effects of the neurotransmitter dopamine. As such, S(−) pramipexole, which is commercially available as Mirapex®, is indicated for treating Parkinson's disease and restless legs syndrome.

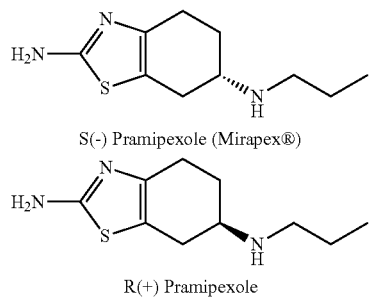

The S(−) pramipexole stereoisomer is a potent agonist of dopamine, with only small daily doses required by patients. Specifically, S(−) pramipexole is a nonergot dopamine agonist with high relative in vitro specificity and full intrinsic activity at the D2 subfamily of dopamine receptors, binding with higher affinity to D3 than to D2 or D4 receptor subtypes. This activity results in, for example, the treatment of the signs and symptoms of Parkinson's disease (e.g., muscle rigidity, tremor, bradykinesia and other motor symptoms). The R(+) pramipexole stereoisomer, on the other hand, does not exhibit the same potent dopamine mimicking property, and may be tolerated in much higher doses. Both enantiomers, shown above, are able to confer neuroprotective effects by their ability to accumulate in brain cells, the spinal cord and mitochondria where they exert a positive effect on neurological function that is independent of the dopamine agonist activity, presumably through inhibition of lipid peroxidation, normalization of mitochondrial function and/or detoxification of oxygen radicals. As such, these compounds may have utility as inhibitors of the cell death cascades and loss of cell viability observed in neurodegenerative diseases. Clinical use of the S(−) pramipexole as a mitochondria-targeted antioxidant is unlikely, however, since the high doses needed for this neuroprotective or anti-oxidative/mitochondrial normalization action are difficult to achieve due to the side effects associated with excessive dopaminergic agonism. In contrast, R(+) pramipexole could be expected to be a clinically useful neuroprotectant due to its low affinity for dopamine receptors. The higher doses of the R(+) pramipexole that may be tolerated by patients without causing adverse side effects will allow greater brain, spinal cord and mitochondrial concentrations to be achieved and increase the degree to which oxidative stress and/or mitochondrial dysfunction may be reduced.

The high doses of R(+) pramipexole, which may be administered to patients will require very pure preparations of the R(+) enantiomer. Current clinical therapeutic doses of pramipexole (Mirapex®) are between 0.125 mg and 4.5 mg per day in order to reduce the frequency of its adverse side effects. As such, compositions of R(+) pramipexole for administration to subjects will need to take into account this upper limit of S(−) enantiomer administration.

Pramipexole appears to increase mitochondrial function in neural cells. For example, pramipexole has been shown to reduce the levels of free radicals produced by the parkinsonian neurotoxin and ETC complex I inhibitor methylpyridinium (MPP+) both in vitro and in vivo and has been reported to block opening of the mitochondrial transition pore (MTP) induced by MPP+ and other stimuli. Furthermore, both enantiomers of pramipexole restored calcein uptake in SH-SY5Y cells treated with MPP+.

In neural cells and an in vivo model of familial amyotrophic lateral sclerosis (ALS), pramipexole and its R(+) enantiomer have been shown to accumulate in mitochondria, to prevent mitochondrial injury, and to restore function.

R(+) pramipexole is a lipophilic cation that has been shown to penetrate cellular membranes and concentrate in mitochondria. Lipophilic cations pass easily through lipid bilayers because their charge is dispersed over a large surface area and the potential gradient drives their accumulation into the mitochondrial matrix. R(+) pramipexole has anti-oxidant activity generally equipotent to that of pramipexole, but lacks pharmacological dopaminergic activity. Therefore, R(+) pramipexole potentially can be administered at higher dosages than pramipexole to achieve an antioxidant effect, while avoiding significant dopamine agonist activity.

Embodiments of the present invention generally relate to pharmaceutical compositions comprising predetermined amounts of R(+) pramipexole and S(−) pramipexole in order to exploit inherent differences in activity that provide additive benefits, including neuroprotective effects, unavailable from the individual enantiomers or a mixture of the enantiomers in equal proportions.

Embodiments of the present invention include compositions comprising R(+) pramipexole and/or S(−) pramipexole. In embodiments, the pramipexole may be a salt of R(+) pramipexole and/or S(−) pramipexole. In additional embodiments, the compositions may further comprise a pharmaceutically acceptable carrier.

Further embodiments of the present invention are directed to multicomponent pharmaceutical compositions comprising a first component and a second component, wherein said first component comprises R(+) pramipexole and said second component comprises S(−) pramipexole. The first and second components may be immediate release formulation, a sustained release formulation or a combination thereof. For example, the first component comprising R(+) pramipexole may be an immediate release formulation and the second component comprising S(−) pramipexole may be an immediate release formulation; the first component comprising R(+) pramipexole may be an immediate release formulation and the second component comprising S(−) pramipexole may be a sustained release formulation; or the first component comprising R(+) pramipexole may be a sustained release formulation and said second component comprising S(−) pramipexole may be an immediate release formulation; or the first component comprising R(+) pramipexole and the second component comprising S(−) pramipexole may both be sustained release formulations. In preferred embodiments, the first component comprising R(+) pramipexole and the second component comprising S(−) pramipexole are both sustained release formulations.

Such multicomponent pharmaceutical compositions may be suitable for enteral or parenteral administration. Examples of enteral administration include, but are not limited to, oral, rectal and intranasal administration. Examples of parenteral administration include, but are not limited to, intravascular administration, subcutaneous injection, and intramuscular administration. Other suitable forms of administration are described in further detail herein.

In preferred embodiments, the multicomponent pharmaceutical composition is suitable for oral administration, and may be formulated into a tablet, a capsule, or a liquid, preferably a tablet or capsule. In one embodiment, the multicomponent pharmaceutical composition may be a multi-layer tablet, such as a bilayer tablet. In another embodiment, the multicomponent pharmaceutical composition may be a multicomponent capsule, such as a divided capsule or a capsule contained within another capsule.

In further embodiments, the multicomponent pharmaceutical compositions may provide for varying release rates of the first and second components. For example, the first component comprising R(+) pramipexole may be released at a first rate and the second component comprising S(−) pramipexole is release at a second rate. The first rate may be faster than said second rate or the first rate may be slower than said second rate.

Further embodiments of the present invention provide multicomponent pharmaceutical compositions comprise as first component comprising a therapeutically effective amount of R(+) pramipexole and a second component comprising a therapeutically effective amount of S(−) pramipexole. The therapeutically effective amount of R(+) pramipexole may be from about 100 milligrams to about 3,000 milligrams, from about 300 milligrams to about 1,500 milligrams, or from about 500 milligrams to about 1,000 milligrams. The therapeutically effective amount of S(−) pramipexole may be from about 0.0625 milligrams to about 6 milligrams, more preferably about 0.375 milligrams to about 4.5 milligrams per day, more preferably about 0.125 milligrams to about 1.5 milligrams, including preferably about 0.125 milligrams, 0.25 milligrams, 0.5 milligrams, 1.0 milligrams and 1.5 milligrams.

In further embodiments of the present invention, the multicomponent pharmaceutical composition may have a chiral purity for the R(+) enantiomer in the first component of 80% or greater, 90% or greater, 95% or greater, 99% or greater, 99.5% or greater, 99.6% or greater, 99.7% or greater, 99.8% or greater, 99.9% or greater, preferably 99.95% or greater and more preferably 99.99% or greater. In more preferred embodiments, the chiral purity for the R(+) enantiomer of pramipexole in the first component of the composition may be 100%.

In further embodiments of the present invention, the multicomponent pharmaceutical composition may have a chiral purity for the S(−) enantiomer in the second component of 80% or greater, 90% or greater, 95% or greater, 99% or greater, 99.5% or greater, 99.6% or greater, 99.7% or greater, 99.8% or greater, 99.9% or greater, preferably 99.95% or greater and more preferably 99.99% or greater. In more preferred embodiments, the chiral purity for the S(−) enantiomer of pramipexole in the second component of the composition may be 100%.

In a preferred embodiment of the present invention, a sustained release pharmaceutical composition comprising S(−) pramipexole and R(+) pramipexole in a sustained release matrix is provided. The R(+) pramipexole may be in a first sustained release matrix and the S(−) pramipexole may be in a second sustained release matrix.

The sustained release pharmaceutical composition may be suitable for enteral administration, including, but not limited to, oral, rectal or intranasal administration. A preferred exemplary formulation is one that is suitable for oral administration, such as, a tablet, a capsule, and a liquid. In other embodiments, the sustained release pharmaceutical composition may be a bilayer tablet or modified capsule. The sustained release pharmaceutical composition may also be suitable for parenteral administration, including, but not limited to, intravascular administration, subcutaneous injection, and intramuscular administration.

In certain embodiments, the sustained release pharmaceutical composition comprises a therapeutically effective amount of R(+) pramipexole. In exemplary embodiments, therapeutically effective amount of R(−) pramipexole is from about 100 milligrams to about 3,000 milligrams; from about 300 milligrams to about 1,500 milligrams; and from about 500 milligrams to about 1,000 milligrams. In certain embodiments, the sustained release pharmaceutical composition comprises a therapeutically effective amount of S(−) pramipexole. In exemplary embodiments, the therapeutically effective amount of S(−) pramipexole is from about 0.0625 milligrams to about 6 milligrams, more preferably about 0.375 milligrams to about 4.5 milligrams per day, more preferably about 0.125 milligrams to about 1.5 milligrams, including preferably about 0.125 milligrams, 0.25 milligrams, 0.5 milligrams, 1.0 milligrams and 1.5 milligrams.

In further embodiments, the sustained release pharmaceutical composition may comprise two different sustained release matrixes. Further, such matrixes may provide for different release rates of R(+) and S(−) pramipexole. For example, the first rate may be faster than the second rate or the first rate is slower than the second rate.

In further embodiments, the sustained release pharmaceutical composition may have a chiral purity for the R(+) enantiomer of pramipexole of 80% or greater; 90% or greater; 95% or greater; 99% or greater; 99.5% or greater, 99.6% or greater, 99.7% or greater, 99.8% or greater, 99.9% or greater, 99.95% or greater; 99.99% or greater; or 100%. In further embodiments, the sustained release pharmaceutical composition may have a chiral purity for the S(−) enantiomer of pramipexole of 80% or greater; 90% or greater; 95% or greater; 99% or greater; 99.5% or greater, 99.6% or greater, 99.7% or greater, 99.8% or greater, 99.9% or greater, 99.95% or greater; 99.99% or greater; or 100%.

Embodiments of the present invention is a pharmaceutical composition comprising a therapeutically effective amount of R(+) pramipexole and a therapeutically effective amount of S(−) pramipexole. The therapeutically effective amounts are preferably effective for providing neuroprotective effects, including the treatment or prevention of Parkinson's disease, the progression thereof or the symptoms thereof. In one embodiment, the therapeutically effective amount of R(+) pramipexole is from about 50 mg to about 5,000 mg, from about 100 mg to about 3,000 mg, preferably from about 300 mg to about 1,500 mg, more preferably from about 500 mg to about 1,000 mg. In a preferred embodiment, the therapeutically effective amount of S(−) is from about 0.0625 milligrams to about 6 milligrams, preferably about 0.0375 to about 4.5 milligrams, more preferably about 0.125 milligrams to about 1.5 milligrams, including preferably about 0.125 milligrams, 0.25 milligrams, 0.5 milligrams, 1.0 milligrams and 1.5 milligrams.

Further embodiments of the present invention relate to dual-release pharmaceutical compositions, wherein the pharmaceutical composition releases a therapeutically effective amount of R(+) pramipexole and a therapeutically effective amount of S(−) pramipexole, or pharmaceutically acceptable salts thereof. In preferred embodiments, the therapeutically effective amount of S(−) pramipexole is an amount that is equal to a NOAEL dose, that is the amount may be an amount below 1.5 mg, below 0.50 mg, or more preferably below 0.05 mg.

Further embodiments of the present invention relate to pharmaceutical compositions comprising R(+) pramipexole and S(−) pramipexole, wherein said pharmaceutical compositions are formulated in such a manner as to take into consideration the need for titrating the dose of S(−) pramipexole when initiating treatment. For example, a pharmaceutical composition comprising a therapeutically effective amount of R(+) pramipexole and an titrating dosage of S(−) pramipexole, wherein said therapeutically effective amount of R(+) pramipexole may be from about 50 mg to about 5,000 mg, from about 100 mg to about 3,000 mg, preferably from about 300 mg to about 1,500 mg, more preferably from about 500 mg to about 1,000 mg and the titrating dosage of S(−) pramipexole may be about 0.125 milligrams; 0.25 milligrams; 0.5 milligrams; 0.75 milligrams; 1.0 milligrams; 1.25 milligrams; and 1.5 milligrams.

Further embodiments related to methods of treating or preventing Parkinson's disease comprising administering such titrating pharmaceutical compositions over a period of time, preferably about seven weeks, and kits containing such pharmaceutical compositions and directions therefore. For example, in one embodiment the method may comprise administering a single pharmaceutical composition containing a therapeutically effective amount of R(+) pramipexole and 0.125 milligrams of S(−) pramipexole about three times a day for about one week. The method may further comprise administering a single pharmaceutical composition containing a therapeutically effective amount of R(+) pramipexole and 0.25 milligrams of S(−) pramipexole about three times a day for about one week following the first week. The method may further comprise administering a single pharmaceutical composition containing a therapeutically effective amount of R(+) pramipexole and 0.5 milligrams of S(−) pramipexole about three times a day for about one week following the second week. The method may further comprise administering a single pharmaceutical composition containing a therapeutically effective amount of R(+) pramipexole and 0.75 milligrams of S(−) pramipexole about three times a day for about one week following the third week. The method may further comprise administering a single pharmaceutical composition containing a therapeutically effective amount of R(+) pramipexole and 1.0 milligrams of S(−) pramipexole about three times a day for about one week following the fourth week. The method may further comprise administering a single pharmaceutical composition containing a therapeutically effective amount of R(+) pramipexole and 1.25 milligrams of S(−) pramipexole about three times a day for about one week following the fifth week. The method may further comprise administering a single pharmaceutical composition containing a therapeutically effective amount of R(+) pramipexole and 1.5 milligrams of S(−) pramipexole about three times a day for about one week following the sixth week. The method may further comprise administering a single pharmaceutical composition containing a therapeutically effective amount of R(+) pramipexole and 1.5 milligrams of S(−) pramipexole about three times a day as a maintenance therapy. The therapeutically effective amount of R(+) pramipexole may be from about 50 mg to about 5,000 mg, from about 100 mg to about 3,000 mg, preferably from about 300 mg to about 1,500 mg, more preferably from about 500 mg to about 1,000 mg. In further embodiments, the therapeutically effective amount of R(+) pramipexole may be constant or may change over the period of treatment.

Another embodiment of the present invention provides a bilayer tablet or caplet. Such a composition can be a two layer tablet or caplet that is formed by pressing one half of the tablet or caplet first, and then pressing the second half of the tablet or caplet onto it. Additionally, other separation tablets can be prepared according to embodiments of the present invention. A tablet within a tablet (compression core tablet) can be prepared. Each portion of the tablet could contain R(+) pramipexole, S(−) pramipexole or a combination thereof, and each portion could be an immediate release or a modified release formulation, and further may be releasable at the same or different rates. Either layer could instead be compressed as a first tablet, with the other layer being compressed on its outside as an outer tablet layer. Furthermore, one of the active ingredients (R(+) pramipexole, S(−) pramipexole or a combination thereof) could be incorporated into a coating solution which can be sprayed onto a core tablet or caplet containing the other active ingredient. Either R(+) pramipexole, S(−) pramipexole or a combination thereof could be used in the coating, with another in the core. Lastly, the particles of R(+) pramipexole, S(−) pramipexole or a combination thereof could be coated with a suitable barrier material, and then prepared into a tablet or capsule. Such bilayer tablets or caplets are described in more detail in U.S. Publication No. 20020177626 entitled "Treatment of Sleep Disturbances" filed Jan. 17, 2002, herein incorporated by reference in its entirety.

Another embodiment of the present invention provides an oral pharmaceutical composition comprising multiple populations of at least one of beads, pellets, tablets and granules provided in a capsule, the composition comprising: a first population of a pharmaceutical active comprising a R(+) pramipexole releasable at a first rate; a population of a basic substance; and a second population of a pharmaceutical active comprising S(−) pramipexole releasable at a second rate. In certain embodiments, the first and second release rates may be the same or different. According to another aspect of the present invention, there is provided an oral pharmaceutical composition comprising multiple populations at least one of beads, pellets, tablets and granules provided in a capsule, the composition comprising: a population of a pharmaceutical active selected from R(+) pramipexole, S(−) pramipexole and a combination thereof; a population of a basic substance; a population of enteric coated pharmaceutical active selected from R(+) pramipexole, S(−) pramipexole and a combination thereof; and a population of enteric coated basic substance. According to another aspect of the present invention, there is provided an oral pharmaceutical composition comprising multiple populations of at least one of beads, pellets, tablets and granules provided in a capsule, the composition comprising: a population of R(+) pramipexole, S(−) pramipexole and a combination thereof; a population of a basic substance; a population of enteric coated R(+) pramipexole, S(−) pramipexole and a combination thereof; and a population of enteric coated basic substance, wherein a separating layer is provided in one or both to separate the R(+) pramipexole and/or S(−) pramipexole or the basic substance from the enteric coating. In aspects, one or more of the populations may further be provided with one or more over-coating layers. Such compositions are described in more detail, for example, in U.S. Publication No. 20040265370 entitled "Oral multi-functional pharmaceutical capsule preparations of proton pump inhibitors" filed Jun. 4, 2004, herein incorporated by reference in its entirety.

In another embodiment of the present invention, there is provided a pharmaceutical composition for delivering one or more pharmaceutically active pramipexole agents that includes: (a) R(+) pramipexole, S(−) pramipexole or a combination thereof covered with an immediate release coating, and (b) R(+) pramipexole, S(−) pramipexole or a combination thereof that are covered with an enteric release coating wherein (1) the enteric release coating has a defined minimum thickness and/or (2) there is a protective layer between the R(+) pramipexole and/or S(−) pramipexole and the enteric release coating and/or (3) there is a protective layer over the enteric release coating. In one embodiment, the immediate release and enteric release portions of the composition are present on the same core. In another embodiment, the immediate release and enteric release components are present on different cores. Such compositions are described in more detail, for example, in U.S. Publication No. 20040219213 entitled "Oral pulsed dose drug delivery system" filed Jan. 16, 2004, herein incorporated by reference in its entirety.

In another embodiment, the R(+) pramipexole, S(−) pramipexole or a combination thereof may be delivered from a delivery device containing separate inner containers of the different drug (gel cap, coated pill or capsule), with the multiple separate containers themselves being contained within an outer container which is ingestible or insertable into a live body, and which outer container is made of a material which is biodegradable after ingestion or insertion into a live body, in which each separate inner container is of a particular standardized shape and size designed to fit closely together with each other, thereby resulting in minimum void space, minimum inert ingredients and maximum amount of active ingredients of medication containable within each inner container, and a standardized outer container shape, size and appearance. The outer container is typically a capsule type device, comprised of two components, with the length of the internal compartment of the said outer container capsule type or cylindrical shaped device being variable to accommodate a variety of volumes of internally contained multiple medications. The active ingredients in each of the inner containers are not in actual physical contact with the active ingredients of any of the other medication products also contained within the outer container. Such delivery devices are described in more detail, for example, in U.S. Publication No. 20050053649 entitled "Medication Delivery Device" filed Feb. 24, 2004, herein incorporated by reference in its entirety.

In a further embodiment, the R(+) pramipexole and the S(−) pramipexole may be in the form of a controlled release dosage form with variable release rates comprising: 1) a bilayer or multilayer tablet core in which at least one of the layers contains one or more pharmaceutically active ingredients and at least one of the layers contains one or more rate controlling polymers; 2) a substantially insoluble casing extended over the tablet core covering the majority of tablet surface but leaving a portion of one layer of the table core exposed (exposed layer), the casing resulting from electrostatic deposition of a powder comprising fusible particles onto the tablet core and fusing the particles to form a thin film. Such dosage forms are described in more detail, for example, in U.S. Publication No. 20060099257 entitled "Controlled Drug Delivery Systems Providing Variable Release Rates" flied Jul. 18, 2002, herein incorporated by reference in its entirety.

Other suitable bilayer tablets are also described in, for example, U.S. Publication Nos. 20050265379, 20050089575, 20050220877, 20060110450, and 20060141037, herein incorporated by reference in their entireties. Other suitable modified release formulations are also described in, for example, U.S. Publication No. 20030049318, herein incorporated by reference in its entirety.

Further compositions of the present invention are also described in U.S. Provisional Application No. 60/894,799 entitled "Modified Release Formulations and Methods of Use of R(+) Pramipexole" filed Mar. 14, 2007, herein incorporated by reference in its entirety. Specifically, the compositions comprising of R(+) pramipexole alone or in combination with S(−) pramipexole, may be formulated into modified release formulations, which are capable of releasing a therapeutically effective amount of the drug over an extended period of time, preferably at least about eight hours, more preferably at least about twelve hours, and even more preferably about twenty-four hours. Delayed release, extended release, controlled release, sustained release and pulsatile release dosage forms and their combinations are types of modified release dosage forms.

Further embodiments of the present invention relate to compositions comprising pramipexole with a chiral purity for the R(+) enantiomer of 80% or greater, 90% or greater, 95% or greater, 99% or greater, preferably 99.5% or greater, 99.6% or greater, 99.7% or greater, 99.8% or greater, 99.9% or greater, more preferably 99.95% or greater and more preferably 99.99% or greater. In more preferred embodiments, the chiral purity for the R(+) enantiomer of pramipexole in the compositions may be 100%.

Embodiments of the present invention also generally relate to the use of the enantiomers of pramipexole in combination to treat or prevent Parkinson's disease and symptoms associated therewith. Preferred embodiments comprise a composition, preferably a pharmaceutical composition, with predetermined amounts of R(+) pramipexole and S(−) pramipexole in order to exploit inherent differences in activity that provide additive benefits, including neuroprotective effects, unavailable from the individual enantiomers or a mixture of the enantiomers in equal proportions.

Embodiments of the present invention are methods of administering a predetermined amount of R(+) pramipexole and a predetermined amount of S(−) pramipexole for the treatment or prevention of Parkinson's disease or symptoms thereof. Preferably the predetermined amounts of each enantiomer are a therapeutically effective amount of each enantiomer. In further embodiments, the predetermined amount of R(+) pramipexole and the predetermined amount of S(−) pramipexole are provided in a pharmaceutical composition.

Further embodiments of the present invention related to methods of treating or preventing Parkinson's disease or the symptoms thereof comprising administering a therapeutically effective amount of R(+) pramipexole and a therapeutically effective amount of S(−) pramipexole. In embodiments, the therapeutically effective amount of R(+) pramipexole may be from about 100 milligrams to about 3,000 milligrams; from about 300 milligrams to about 1,500 milligrams; and from about 500 milligrams to about 1,000 milligrams. In further embodiments, the therapeutically effective amount of S(−) pramipexole is from about 0.0625 milligrams to about 6 milligrams, preferably about 0.0375 to about 4.5 milligrams, more preferably about 0.125 milligrams to about 1.5 milligrams, including preferably about 0.125 milligrams, 0.25 milligrams, 0.5 milligrams, 1.0 milligrams and 1.5 milligrams. The therapeutically effective amount of R(+) pramipexole and and S(−) pramipexole may be administered, for example, from one to five times a day, more preferably three times a day, even more preferably two times or once a day. The therapeutically effective amount of R(+) pramipexole and S(−) pramipexole may be administered in a single pharmaceutical composition. The pharmaceutical composition may be an immediate release composition, or more preferably a sustained release composition.

In further embodiments of such methods, the R(+) pramipexole may have a chiral purity for the R(+) enantiomer of pramipexole of 80% or greater; 90% or greater; 95% or greater; 99% or greater; preferably 99.5% or greater, 99.6% or greater, 99.7% or greater, 99.8% or greater, 99.9% or greater, more preferably 99.95% or greater and more preferably 99.99% or greater. In more preferred embodiments, the chiral purity for the R(+) enantiomer of pramipexole in the compositions may be 100%. In further embodiments of such methods, the S(-) pramipexole may have a chiral purity for the S(-) enantiomer of pramipexole of 80% or greater; 90% or greater; 95% or greater; 99% or greater; preferably 99.5% or greater, 99.6% or greater, 99.7% or greater, 99.8% or greater, 99.9% or greater, more preferably 99.95% or greater and more preferably 99.99% or greater. In more preferred embodiments, the chiral purity for the S(-) enantiomer of pramipexole in the compositions may be 100%.

Further embodiments of the present invention relate to methods of using or administering R(+) pramipexole for the treatment and/or prevention of Parkinson's disease and symptoms associated with Parkinson's disease. In preferred embodiments, the methods include administering a pharmaceutical composition comprising R(+) pramipexole, more preferably a pharmaceutical composition with a chiral purity for the R(+) enantiomer of 80% or greater, 90% or greater, 95% or greater, 99% or greater, preferably 99.5% or greater, 99.6% or greater, 99.7% or greater, 99.8% or greater, 99.9% or greater, more preferably 99.95% or greater and more preferably 99.99% or greater, or more preferably 100%.

Another preferred embodiment of the present invention is to method of treating or preventing Parkinson's disease or the symptoms thereof comprising administering a therapeutically effective amount of R(+) pramipexole and a therapeutically effective amount of S(-) pramipexole. Preferably, the R(+) pramipexole and the S(-) pramipexole are administered in a single composition, but may be administered in separate compositions. The therapeutically effective amounts are preferably effective for providing neuroprotective effects, including the treatment or prevention of Parkinson's disease, the progression thereof or the symptoms thereof. In one embodiment, the therapeutically effective amount of R(+) pramipexole is from about 0.1 mg/kg/day to about 1,000 mg/kg/day, from about 1 mg/kg/day to about 100 mg/kg/day, preferably from about 3 mg/kg/day to about 70 mg/kg/day, more preferably from about 7 mg/kg/day to about 40 mg/kg/day. In a preferred embodiment, the therapeutically effective amount of S(-) is from about 0.0625 milligrams to about 6 milligrams, more preferably about 0.375 milligrams to about 4.5 milligrams per day, more preferably about 0.125 milligrams to about 1.5 milligrams, including preferably about 0.375 milligrams per day, 0.75 milligrams per day, about 0.125 milligrams, 0.25 milligrams, 0.5 milligrams, 1.0 milligrams and 1.5 milligrams, 2.25 milligrams per day, 3.0 milligrams per day, 3.75 milligrams per day, 4.5 milligrams per day and 6 milligrams per day.

In one embodiment, a method of treating or preventing Parkinson's disease comprising administering R(+) pramipexole is provided. The R(+) pramipexole may be administered in a composition, preferably a pharmaceutical composition, containing a therapeutically effective amount of R(+) pramipexole. More preferably, the method comprises administering a pharmaceutical composition comprising a therapeutically effective amount of R(+) pramipexole with a chiral purity for the R(+) enantiomer of greater than 80%, preferably greater than 90%, more preferably greater than 95%, and most preferably greater than 99%, including 99.5% or greater, 99.6% or greater, 99.7% or greater, 99.8% or greater, 99.9% or greater, preferably 99.95% or greater and more preferably 99.99% or greater, or 100%. The therapeutically effective amount of R(+) pramipexole may be from about 50 milligrams to about 5000 milligrams, about 100 milligrams to about 3000 milligrams, preferably from about 300 milligrams to about 1500 milligrams, more preferably from about 500 milligrams to about 1000 milligrams. The pharmaceutical composition may be suitable for oral administration. In other embodiments, the pharmaceutical composition may contain a no observable adverse effect level amount of S(-) pramipexole or a non-effective dose amount of S(-) pramipexole. In another embodiment, the pharmaceutical composition consists essentially of R(+) pramipexole.

Embodiments of the invention include compositions that may be administered orally, preferably as a solid oral dose, and more preferably as a solid oral dose that may be a capsule or tablet. In preferred embodiments, the compositions of the present invention may be formulated as tablets for oral administration.

Embodiments of the invention include pharmaceutical compositions comprising R(+) pramipexole and a no observable adverse effect level (NOAEL) dose amount of S(-) pramipexole. The pharmaceutical compositions of embodiments may be effective as inhibitors of oxidative stress, inhibitors of lipid peroxidation, in the detoxification of oxygen radicals and as neuroprotectants. In embodiments, the NOAEL dose amount of S(-) pramipexole may be an amount that does not exceed 1.50 mg. In additional embodiments, the NOAEL dose amount of S(-) pramipexole may be an amount that does not exceed 0.5 mg, more preferably 0.05 mg.

Additional embodiments of the invention include a pharmaceutical composition comprising a therapeutically effective amount of R(+) pramipexole and a NOAEL dose amount of S(-) pramipexole.

Each of the foregoing preferred embodiments may employ the use of compositions comprising pramipexole which is chirally pure for the R(+) and/or the S(-) enantiomer, or pharmaceutically acceptable salts thereof. The compositions may be administered to subjects in doses that range from between 0.1 mg/kg/day to 1,000 mg/kg/day. Preferably, the compositions may be administered in doses of R(+) pramipexole from about 50 mg to about 5,000 mg, from about 100 mg to about 3,000 mg, from about 300 mg to about 1,500 mg, or from about 500 mg to about 1,000 mg. These doses of pramipexole preferably are in preparations which have a chemical purity of 97% or greater and a chiral purity for the R(+) enantiomer of 99.6% or greater, 99.7% or greater, 99.8% or greater, 99.9% or greater, preferably 99.95% or greater and more preferably 99.99% or greater. In a preferred embodiment, the compositions comprising pramipexole, or a pharmaceutically acceptable salt thereof, may have a chiral purity for the R(+) enantiomer of 100%. The compositions may further comprise a carrier. The compositions of the present invention may be administered orally, preferably as a solid oral dose, and more preferably as a solid oral dose that may be a capsule or tablet. In preferred embodiments, the compositions of the present invention may be formulated as tablets for oral administration.

The need for pramipexole compositions which are of such high chiral purity for the R(+) and S(−) enantiomers is apparent from the experimental data disclosed herein (see Examples and Tables 3 and 4). Previous data in the literature indicated that the R(+) enantiomer of pramipexole is 10 to 200-fold less active as a dopamine receptor agonist than the S(−) enantiomer. Unexpectedly this reported ratio may greatly underestimate the different affinities of the R(+) and S(−) enantiomers of pramipexole for the dopamine receptors (see Examples), and thereby fails to appreciate the degree of chiral purity necessary to make R(+) pramipexole practical or suitable as a therapeutic composition. In fact, as shown in Table 3, the R(+) enantiomer may be more than 5,000-fold less active as a dopamine agonist than the S(−) enantiomer of pramipexole (Table 3). Furthermore, in animal studies, the NOAEL dose for the R(+) enantiomer is 20,000-fold greater than for the S(−) enantiomer (Table 4). Thus, for compositions of pramipexole which are chirally pure for the R(+) enantiomer, even a small (fractional percentage) contamination with the S(−) enantiomer may have observable and predictable adverse consequences.

While not wishing to be bound by theory, these data (see Examples and Tables 3 and 4) present a number of interesting possibilities. Initially, the data demonstrate the high (approaching absolute) chiral purity of the pramipexole compositions for the R(+) enantiomer. R(+) pramipexole is administered in high dose levels in the studies disclosed herein (equivalent to human doses of 1,000 mg to 3,000 mg; see Examples), so that even the smallest amount of S(−) pramipexole would contribute to the observed NOAEL and MTD. For example, with reference to human equivalence doses based on data obtained in dogs, the MTD for the R(+) enantiomer has been shown to be equivalent to about 3,000 mg for a 70 kg human subject, while the equivalent MTD for the S(−) enantiomer would be equivalent to only 0.30 mg for that same subject (Table 4). That is a difference of 10,000-fold. As mentioned above, the NOAEL dose for the R(+) enantiomer is 20,000-fold greater than for the S(−) enantiomer (Table 4). Thus, the R(+) pramipexole compositions used in these studies must be at least 99.99% pure it one were to assume that the observed side effects stemmed only from contamination by the S(−) enantiomer. On the other hand, these data demonstrate the high dose levels of the R(+) enantiomer of pramipexole that may be administered safely. These data highlight the importance of the high chiral purity for the R(+) enantiomer of pramipexole that may be used in various aspects of the present invention.

The S(−) pramipexole and the R(+) pramipexole of the present invention may be synthesized and/or purified by methods disclosed in the copending U.S. Provisional Application No. 60/894,829 entitled "Methods of Synthesizing and Purifying R(+) and S(−) pramipexole", filed Mar. 14, 2007, and U.S. Provisional Application No. 60/894,814 entitled "Methods of Enantiomerically Purifying Chiral Compounds", filed Mar. 14, 2007, which are incorporated herein by reference in their entireties. Specifically, preparations of pramipexole which are chirally pure for the R(+) or the S(−) enantiomer may be produced using a bimolecular nucleophilic substitution ($S_N2$) reaction. The process comprises dissolving a diamine of formula 2,6 diamino-4,5,6,7-tetrahydrobenzothiazole in an organic solvent, reacting the diamine with a propyl sultanate or a propyl halide under conditions sufficient to generate and precipitate the pramipexole salt, and recovering the pramipexole salt. In an embodiment, the propyl sulfonate may be propyl tosylate. The conditions sufficient to generate and precipitate the pramipexole salt comprise using dimethylformamide as the organic solvent and heating the dissolved diamine at an elevated temperature. A mixture of propyl sulfonate or propyl halide, preferably about 1.25 molar equivalents, dissolved in dimethylformamide, preferably at about 10 volumes, and di-isoproplyethylamine, preferably at about 1.25 molar equivalents, is added slowly to the heated diamine with stirring over a period of several hours. Alternatively, the di-isoproplyethylamine may be added to the reaction with the diamine, and the propyl sulfonate or propyl halide may he dissolved in dimethylformamide to form a mixture, which may be added to the reaction with stirring for several hours. The elevated temperature of the reaction may be about 65° C. or lower. The times necessary for the reaction may vary with the identities of the reactants, the solvent system and with the chosen temperature, and may be understood by one skilled in the art.

Embodiments of the process further comprise cooling the reaction to about room temperature and stirring the reaction for several hours. The process may further involve filtering the reaction to isolate a solid precipitate, washing the precipitate with an alcohol, and drying the precipitate under vacuum. The pramipexole salt reaction product of this process displays a high chemical purity and an increased optical purity over the reactants. Without wishing to be bound by theory, the increased optical purity may be due to limited solubility of the pramipexole salt reaction product in the polar solvents of the reaction mixture. Purification of the final pramipexole reaction product from the reaction mixture thus involves simple trituration and washing of the precipitated pramipexole salt in a volatile solvent such as an alcohol or heptane, followed by vacuum drying.

The chemical and chiral purity of the preparations of R(+) or the S(−) pramipexole may be verified with at least HPLC, $^{13}C$-NMR, $^1H$-NMR and FTIR. In preferred embodiments, the R(+) pramipexole may be synthesized by the method described above, which yields enantiomerically pure material. Alternatively, the R(+) or S(−) pramipexole may be purified from mixtures of R(+) and S(−) pramipexole using a purification scheme which is disclosed in U.S. Provisional Application No. 60/894,829 entitled "Methods of Synthesizing and Purifying R(+) and S(−) pramipexole", filed Mar. 14, 2007, and U.S. Provisional Application No. 60/894,814 entitled "Methods of Enantiomerically Purifying Chiral Compounds", filed Mar. 14, 2007, which are incorporated herein by reference in their entireties. Pramipexole, which is chirally pure for the R(+) or the S(−) enantiomer, may be triturated from an enantiomerically enriched pramipexole acid addition solution based on insolubility of the enantiomeric salts in the resulting achiral reagents. Embodiments of the process comprise dissolving pramipexole which is enantiomerically enriched for the R(+) or the S(−) enantiomer in an organic solvent at an elevated temperature, adding from about 1.0 molar equivalents to about 2.0 molar equivalents of a selected acid, cooling the reaction to room temperature, stirring the cooled reaction at room temperature for an extended time and recovering enantiomerically pure R(+) or S(−) pramipexole.

The chirally pure R(+) or S(−) pramipexole prepared by either of the above methods may be converted to a pharmaceutically acceptable salt of R(+) or S(−) pramipexole. For example, dihydrochloride is a preferred pharmaceutical salt due its high water solubility. The dihydrochloride salt may be prepared from other salts of the pramipexole in a one step method comprising reacting an enantiomer of pramipexole, or a salt, with concentrated HCl in an organic solvent, such as an alcohol, at a reduced temperature. A preferred reduced temperature is a temperature of from about 0° C. to about 5° C. An organic solvent, such as methyl tert-butyl ether, may be added, and the reaction may be stirred for an additional hour. The pramipexole dihydrochloride product may be recovered from the reaction mixture by filtering, washing with an alcohol and vacuum drying.

Each of the methods disclosed herein for the manufacture and purification of S(−) pramipexole and R(+) pramipexole or a pharmaceutically acceptable salt thereof may be scalable to provide industrial scale quantities and yields, supplying products with both high chemical and chiral purity. As such, in preferred embodiments, enantiomerically pure R(+) or S(−) pramipexole may be manufactured in large batch quantities as may be required to meet the needs of a large scale pharmaceutical use.

The high chiral purity of the pramipexole used herein, R(+) and the S(−) pramipexole, allows for therapeutic compositions that may have a wide individual and daily dose range. In one embodiment, the compositions of R(+) and S(−) pramipexole may be used to treat neurodegenerative diseases, or other diseases associated with mitochondrial dysfunction or increased oxidative stress. The compositions of the present invention may also be useful in the treatment of other disorders not listed herein, and any listing provided in this invention is for exemplary purposes only and is non-limiting.

Thus, the neuroprotective effect of the compositions of the present invention may derive at least in part from the ability of the R(+) enantiomer of pramipexole to prevent neural cell death by at least one of three mechanisms. First, the R(+) enantiomer of pramipexole may be capable of reducing the formation of reactive oxygen species in cells with impaired mitochondrial energy production. Second, the R(+) enantiomer of pramipexole may partially restore the reduced mitochondrial membrane potential that has been correlated with Alzheimer's disease, Parkinson's disease and amyotrophic lateral sclerosis diseases. Third, the R(+) enantiomer of pramipexole may block the cell death pathways which are produced by pharmacological models of Alzheimer's disease, Parkinson's disease, amyotrophic lateral sclerosis diseases and mitochondrial impairment.

As such, an embodiment of the invention is a composition comprising R(+) pramipexole alone or in combination with S(−) pramipexole, or pharmaceutically acceptable salts thereof. The composition may further comprise a pharmaceutically acceptable carrier. An additional embodiment of the invention is a composition comprising a therapeutically effective amount of R(+) pramipexole alone or in combination with S(−) pramipexole, or pharmaceutically acceptable salts thereof. The composition may further comprise a pharmaceutically acceptable carrier. An additional embodiment of the invention is a composition comprising a therapeutically effective amount of R(+) pramipexole, or a pharmaceutically acceptable salt thereof, and a no observable adverse effect level (NOAEL) amount of S(−) pramipexole. The therapeutic composition may further comprise a pharmaceutically acceptable carrier. The compositions of the invention may be administered orally, preferably as a solid oral dose, and more preferably as a solid oral dose that may be a capsule or tablet. In preferred embodiments, the compositions of the present invention may be formulated as tablets for oral administration.

An additional embodiment of the invention is a composition useful as a neuroprotectant comprising a therapeutically effective amount of R(+) pramipexole, or a pharmaceutically acceptable salt thereof, and a therapeutically effective amount of S(−) pramipexole, or a pharmaceutically acceptable salt thereof. The composition may further comprise a pharmaceutically acceptable carrier. The composition may be useful in the treatment of diseases which may be alleviated by the action of a neuroprotectant. An additional embodiment of the invention is a therapeutic composition suitable for use as a neuroprotectant comprising a therapeutically effective amount of R(+) pramipexole, or a pharmaceutically acceptable salt thereof, and a therapeutically effective amount of S(−) pramipexole, or a pharmaceutically acceptable salt thereof. The composition may further comprise a pharmaceutically acceptable carrier. The therapeutic composition may be useful in the treatment of diseases related to neuronal degeneration or neuronal cell death.

The compositions of these several embodiments which comprise of R(+) pramipexole alone or in combination with S(−) pramipexole as an active agent may be effective as inhibitors of oxidative stress, inhibitors of lipid peroxidation, in the detoxification of oxygen radicals, and the normalization of mitochondrial function. Further, they may be effective as treatment for impaired motor function, and in degenerative diseases that may affect cardiac and striated muscle and retinal tissues.

Yet another embodiment of the invention is a method for treating a neurodegenerative disease by administering a therapeutically effective amount of R(+) pramipexole alone or in combination with S(−) pramipexole. In accordance with this embodiment, the of R(+) pramipexole alone or in combination with S(−) pramipexole may be formulated as a pharmaceutical or therapeutic composition by combining with one or more pharmaceutically acceptable carriers. Embodiments include pharmaceutical or therapeutic compositions that may be administered orally, preferably as a solid oral dose, and more preferably as a solid oral dose that may be a capsule or tablet. In a preferred embodiment, the pharmaceutical or therapeutic composition is formulated in tablet or capsule form for use in oral administration routes. The compositions and amounts of non-active ingredients in such a formulation may depend on the amount of the active ingredient, and on the size and shape of the tablet or capsule. Such parameters may be readily appreciated and understood by one of skill in the art.

The pharmaceutical or therapeutic compositions may be prepared, packaged, sold in bulk, as a single unit dose, or as multiple unit doses.

For the purposes of this invention, a "salt" of the S(−) pramipexole and/or R(+) pramipexole as used herein is any acid addition salt, preferably a pharmaceutically acceptable acid addition salt, including but not limited to, halogenic acid salts such as, for example, hydrobromic, hydrochloric, hydrofluoric and hydroiodic acid salt; an inorganic acid salt such as, for example, nitric, perchloric, sulfuric and phosphoric acid salt; an organic acid salt such as, for example, sulfonic acid salts (methanesulfonic, trifluoromethan sulfonic, ethanesulfonic, benzenesulfonic or p-toluenesulfonic), acetic, malic, fumaric, succinic, citric, benzoic, gluconic, lactic, mandelic, mucic, pamoic, pantothenic, oxalic and maleic acid salts; and an aminoacid salt such as aspartic or glutamic acid salt. The acid addition salt may be a mono or di-acid addition salt, such as a di-hydrohalogenic, di-sulfuric, di-phosphoric or di-organic acid salt. In all cases, the acid addition salt is used as an achiral reagent which is not selected on the basis of any expected or known preference for interaction with or precipitation of a specific optical isomer of the products of this invention (e.g. as opposed to the specific use of D(+) tartaric acid in the prior art, which may preferentially precipitate the R(+) enantiomer of pramipexole).

"Pharmaceutically acceptable salt" is meant to indicate those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al. (1977) J. Pharm. Sciences, Vol 6. 1-19, describes pharmaceutically acceptable salts in detail.

The compositions may be formulated to be administered orally, ophthalmically, intravenously, intramuscularly, intra-arterially, intramedularry, intrathecally, intraventricularly, transdermally, subcutaneously, intraperitoneally, intravesicularly, intranasally, enterally, topically, sublingually, or rectally. In embodiments, the therapeutically effective amount of R(+) pramipexole may be from about 0.1 mg/kg/day to about 1,000 mg/kg/day or from about 1 mg/kg/day to about 100 mg/kg/day. In preferred embodiments, the therapeutically effective amount of R(+) pramipexole may be from about 3 mg/kg/day to about 70 mg/kg/day. In more preferred embodiments, the therapeutically effective amount of R(+) pramipexole may be from about 7 mg/kg/day to about 40 mg/kg/day. In embodiments, the therapeutically effective amount of R(+) pramipexole may be from about 50 mg to about 5,000 mg, from about 100 mg to about 3,000 mg, preferably from about 300 mg to about 1,500 mg, or more preferably from about 500 mg to about 1,000 mg.

In embodiments of the present invention, the NOAEL dose amount of S(−) pramipexole is an amount that does not exceed 1.5 mg, does not exceed 0.5 mg, or more preferably does not exceed 0.05 mg. In another preferred embodiment, the NOAEL dose amount of S(−) pramipexole is an amount that does not exceed 0.0007 mg/kg per unit dose.

The compositions of pramipexole may have a chiral purity for the particular enantiomer of at least 99.5%, preferably at least 99.6%, preferably at least 99.7%, preferably at least 99.8%, preferably at least 99.9%, preferably at least 99.95% and more preferably at least 99.99%. In a preferred embodiment, the chiral purity for the enantiomer of pramipexole, or pharmaceutically acceptable salt thereof, may be 100%. In embodiments, the composition may further comprise a pharmaceutically acceptable carrier.

Embodiments of the invention include compositions that may be administered orally, preferably as a solid oral dose, and more preferably as a solid oral dose that may be a capsule or tablet. In preferred embodiments, the compositions of the present invention may be formulated as tablets for oral administration.

Another embodiment of the invention is a composition consisting essentially of a therapeutically effective amount of R(+) pramipexole and a NOAEL dose amount of S(−) pramipexole. Another embodiment of the invention is a composition consisting of a therapeutically effective amount of R(+) pramipexole and a NOAEL dose amount of S(−) pramipexole. Such compositions may preferably be therapeutic or pharmaceutical compositions.

Another embodiment of the invention is a pharmaceutical composition comprising a therapeutically effective amount of R(+) pramipexole and to NOAEL dose amount of S(−) pramipexole administered in a unit dose form. Preferable unit dose forms include those suitable for oral administration, including but not limited to, capsules, tablets and the like. Table 1 shows various exemplary embodiments. Shown in each column of Table 1 is the amount of S(−) pramipexole that may be co-administered in a NOAEL dose amount as a function of the chiral purity of the composition for the R(+) enantiomer of pramipexole. The therapeutically effective amount of R(+) pramipexole may preferably be about 50 mg to about 5,000 mg, preferably from about 100 mg to about 3,000 mg, preferably from about 300 mg to about 1,500 mg, more preferably from about 500 mg to about 1,000 mg. This dose may be administered as a single daily dose, or may be divided into several doses administered throughout the day, for example 1 to 5 doses per day. The NOAEL dose of S(−) pramipexole may be preferably below 1.5 mg, preferably below 0.5 mg, or more preferably below 0.05 mg. Thus, as a non-limiting example, an embodiment of the invention may be a dose of 1,500 mg/day administered to a patient as a single unit dose which may have a chiral purity for the R(+) enantiomer of pramipexole that is at least about 99.967% so that the non-adverse dose of S(−) pramipexole may remain below 0.50 mg/dose. Alternatively, a dose of 1,500 mg/day administered to a patient as three individual doses of 500 mg may have a chiral purity of the R(+) pramipexole that is at least about 99.90% so that the non-adverse dose of S(−) pramipexole may remain below 0.50 mg/dose or 1.5 mg/day. With reference to Table 1, any combination of chiral purity and unit dose may be used which allows for the desired combination of a therapeutically effective amount of R(+) pramipexole and a therapeutically effective amount, but a non-adverse effect dose amount of S(−) pramipexole as stated herein.

Another embodiment of the invention is a pharmaceutical composition formulated as a tablet suitable for oral administration comprising an amount of R(+) pramipexole greater than 50 mg and a NOAEL dose amount of S(−) pramipexole that is less than 0.05 mg, preferably an amount of R(+) pramipexole greater than 100 mg and a NOAEL dose amount of S(−) pramipexole that is less than 0.05 mg, and more preferably an amount of R(+) pramipexole greater than 250 mg and a NOAEL dose amount of S(−) pramipexole that is less than 0.05 mg. Another preferred embodiment is a pharmaceutical composition formulated as a tablet suitable for oral administration comprising an amount of R(+) pramipexole greater than 500 mg and a NOAEL dose amount of S(−) pramipexole that is less than 0.05 mg.

TABLE 1

Preferred no observable adverse effect level doses of S(−) pramipexole based on the chiral purity of the composition for R(+) pramipexole

| Percent Chiral Purity | Unit Dose Amount of R(+) pramipexole (mg) | | | | | | | | | | | | |
|---|---|---|---|---|---|---|---|---|---|---|---|---|---|
|  | 20 | 25 | 30 | 50 | 75 | 100 | 120 | 150 | 200 | 250 | 500 | 1000 | 1500 |
| 99.9967 | 0.001 | 0.001 | 0.001 | 0.002 | 0.002 | 0.003 | 0.004 | 0.005 | 0.007 | 0.008 | 0.017 | 0.033 | 0.050 |
| 99.9958 | 0.001 | 0.001 | 0.001 | 0.002 | 0.003 | 0.004 | 0.005 | 0.006 | 0.008 | 0.010 | 0.021 | 0.042 | 0.062 |
| 99.9950 | 0.001 | 0.001 | 0.002 | 0.002 | 0.004 | 0.005 | 0.006 | 0.007 | 0.010 | 0.012 | 0.025 | 0.050 | 0.075 |
| 99.9933 | 0.001 | 0.002 | 0.002 | 0.003 | 0.005 | 0.007 | 0.008 | 0.010 | 0.013 | 0.017 | 0.033 | 0.067 | 0.100 |
| 99.9900 | 0.002 | 0.003 | 0.003 | 0.005 | 0.008 | 0.010 | 0.012 | 0.015 | 0.020 | 0.025 | 0.050 | 0.100 | 0.150 |
| 99.9833 | 0.003 | 0.004 | 0.005 | 0.008 | 0.013 | 0.017 | 0.020 | 0.025 | 0.033 | 0.042 | 0.084 | 0.167 | 0.250 |
| 99.9800 | 0.004 | 0.005 | 0.006 | 0.010 | 0.015 | 0.020 | 0.024 | 0.030 | 0.040 | 0.050 | 0.100 | 0.200 | 0.300 |
| 99.9750 | 0.005 | 0.006 | 0.008 | 0.013 | 0.019 | 0.025 | 0.030 | 0.038 | 0.050 | 0.063 | 0.125 | 0.250 | 0.375 |
| 99.9667 | 0.007 | 0.008 | 0.010 | 0.017 | 0.025 | 0.033 | 0.040 | 0.050 | 0.067 | 0.083 | 0.167 | 0.333 | 0.500 |
| 99.9583 | 0.008 | 0.010 | 0.013 | 0.021 | 0.031 | 0.042 | 0.050 | 0.063 | 0.083 | 0.104 | 0.208 | 0.417 | 0.625 |
| 99.9500 | 0.010 | 0.012 | 0.015 | 0.025 | 0.037 | 0.050 | 0.060 | 0.075 | 0.100 | 0.125 | 0.250 | 0.500 | 0.750 |
| 99.9333 | 0.013 | 0.017 | 0.020 | 0.033 | 0.050 | 0.067 | 0.080 | 0.100 | 0.133 | 0.167 | 0.333 | 0.667 | 1.000 |
| 99.9000 | 0.020 | 0.025 | 0.030 | 0.050 | 0.075 | 0.100 | 0.120 | 0.150 | 0.200 | 0.250 | 0.500 | 1.000 | 1.500 |
| 99.8333 | 0.033 | 0.042 | 0.050 | 0.083 | 0.125 | 0.167 | 0.200 | 0.250 | 0.333 | 0.417 | 0.834 | 1.667 | 2.500 |
| 99.8000 | 0.040 | 0.050 | 0.060 | 0.100 | 0.150 | 0.200 | 0.240 | 0.300 | 0.400 | 0.500 | 1.000 | 2.000 | 3.000 |
| 99.7500 | 0.050 | 0.063 | 0.075 | 0.125 | 0.188 | 0.250 | 0.300 | 0.375 | 0.500 | 0.625 | 1.250 | 2.500 | 3.750 |
| 99.6667 | 0.067 | 0.083 | 0.100 | 0.167 | 0.250 | 0.333 | 0.400 | 0.500 | 0.667 | 0.833 | 1.667 | 3.333 | 5.000 |
| 99.5800 | 0.084 | 0.105 | 0.126 | 0.210 | 0.315 | 0.420 | 0.500 | 0.630 | 0.840 | 1.050 | 2.100 | 4.200 | 6.300 |
| 99.5000 | 0.100 | 0.125 | 0.150 | 0.250 | 0.375 | 0.500 | 0.600 | 0.750 | 1.000 | 1.250 | 2.500 | 5.000 | 7.500 |
| 99.3333 | 0.133 | 0.167 | 0.200 | 0.333 | 0.500 | 0.667 | 0.800 | 1.000 | 1.333 | 1.667 | 3.334 | 6.667 | 10.00 |
| 99.0000 | 0.200 | 0.250 | 0.300 | 0.500 | 0.750 | 1.000 | 1.200 | 1.500 | 2.000 | 2.500 | 5.000 | 10.00 | 15.00 |
| 98.3300 | 0.334 | 0.418 | 0.500 | 0.835 | 1.253 | 1.670 | 2.004 | 2.505 | 3.340 | 4.175 | 8.350 | 16.70 | 25.00 |
| 98.0000 | 0.400 | 0.500 | 0.600 | 1.000 | 1.500 | 2.000 | 2.400 | 3.000 | 4.000 | 5.000 | 10.00 | 20.00 | 30.00 |
| 97.5000 | 0.500 | 0.625 | 0.750 | 1.250 | 1.875 | 2.500 | 3.000 | 3.750 | 5.000 | 6.250 | 12.50 | 25.00 | 37.50 |

A preferred no observation adverse effect level (NOAEL) dose amount of the S(−) pramipexole may be below 0.5 mg, preferably below 0.05 mg.

The compounds of the present invention can be administered in the conventional manner by any route where they are active. Administration can be systemic, topical, or oral. For example, administration can be, but is not limited to, parenteral, subcutaneous, intravenous, intramuscular, intraperitoneal, transdermal, oral, buccal, or ocular routes, or intravaginally, intravesicularly, by inhalation, by depot injections, or by implants. Thus, modes of administration for the compounds of the present invention (either alone or in combination with other pharmaceuticals) can be, but are not limited to, sublingual, injectable (including short-acting, depot, implant and pellet forms injected subcutaneously or intramuscularly), or by use of vaginal creams, suppositories, pessaries, vaginal rings, rectal suppositories, intrauterine devices, and transdermal forms such as patches and creams.

The doses of the R(+) pramipexole which may be administered to a patient in need thereof may range between about 0.1 mg/kg per day and about 1,000 mg/kg per day. This dose may be administered as a single daily dose, or may be divided into several doses which are administered throughout the day, such as 1 to 5 doses. The route of administration may include oral, sublingual, transdermal, rectal, or any accessible parenteral route. One of ordinary skill in the art will understand and appreciate the dosages and timing of said dosages to be administered to a patient in need thereof. The doses and duration of treatment may vary, and may be based on assessment by one of ordinary skill in the art based on monitoring and measuring improvements in neuronal and non-neuronal tissues. This assessment may be made based on outward physical signs of improvement, such as increased muscle control, or on internal physiological signs or markers. The doses may also depend on the condition or disease being treated, the degree of the condition or disease being treated and further on the age and weight of the patient.

Specific modes of administration will depend on the indication. The selection of the specific route of administration and the dose regimen may be adjusted or titrated by the clinician according to methods known to the clinician in order to obtain the optimal clinical response. The amount of compound to be administered may be that amount which is therapeutically effective. The dosage to be administered may depend on the characteristics of the subject being treated, e.g., the particular animal or human subject treated, age, weight, health, types of concurrent treatment, if any, and frequency of treatments, and can be easily determined by one of skill in the art (e.g., by the clinician).

A preferable route of administration of the compositions of the present invention may be oral, with a more preferable route being in the form of tablets, capsules, lozenges and the like. In preferred embodiments, the compositions of the present invention may be formulated as tablets for oral administration. A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent.

The tablets may be uncoated or they may be coated by known techniques, optionally to delay disintegration and absorption in the gastrointestinal tract and thereby providing a sustained action over a longer period. The coating may be adapted to release the active compound in a predetermined pattern (e.g., in order to achieve a controlled release formulation) or it may be adapted not to release the active compound until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material such as, e.g., glyceryl monostearate or glyceryl distearate may be employed. The solid tablet compositions may include a coating adapted to protect the composition from unwanted chemical changes, (e.g., chemical degradation prior to the release of the active drug substance).

Pharmaceutical formulations containing the compounds of the present invention and a suitable carrier may also be any number of solid dosage forms which include, but are not limited to, tablets, capsules, cachets, pellets, pills, powders and granules; topical dosage forms which include, but are not limited to, solutions, powders, fluid emulsions, fluid suspensions, semi-solids, ointments, pastes, creams, gels and jellies, and foams; and parenteral dosage forms which include, but are not limited to, solutions, suspensions, emulsions, and dry powder; comprising an effective amount of a polymer or copolymer of the present invention. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, *Modern Pharmaceutics*, Banker & Rhodes, Marcel Dekker, Inc. (1979); and *Goodman & Gilman's The Pharmaceutical Basis of Therapeutics*, 6th Edition, MacMillan Publishing Co., New York (1980) can be consulted.

The compounds of the present invention can be formulated for parenteral administration by injection, e.g., by bolus injection or continuous infusion. The compounds can be administered by continuous infusion over a period of about 15 minutes to about 24 hours. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

For oral administration, the compounds can be formulated readily by combining these compounds with pharmaceutically acceptable carriers well known in the art. As used herein, the term "pharmaceutically acceptable carrier" means a non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as, e.g., lactose, binders such as, e.g., starches, and/or lubricants such as, e.g., talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

For buccal or sublingual administration, the compositions can take the form of tablets, flash melts or lozenges formulated in any conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The compounds of the present invention can also be formulated in rectal compositions such as suppositories or retention enemas, e.g., containing conventional suppository bases such as cocoa butter or other glycerides.

In addition to the formulations described previously, the compounds of the present invention can also be formulated as a depot preparation. Such long acting formulations can be administered by implantation (for example subcutaneously or intramuscularly) or by intramuscular injection.

Depot injections can be administered at about 1 to about 6 months or longer intervals. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

In transdermal administration, the compounds of the present invention, for example, can be applied to a plaster, or can be applied by transdermal, therapeutic systems that are consequently supplied to the organism.

Pharmaceutical and therapeutic compositions of the compounds also can comprise suitable solid or gel phase carriers or excipients. Examples of such carriers or excipients include but are not limited to calcium carbonate, calcium phosphate, various sugars, starches, cellulose derivatives, gelatin, and polymers such as, e.g., polyethylene glycols.

The compounds of the present invention can also be administered in combination with other active ingredients, such as, for example, adjuvants, protease inhibitors, or other compatible drugs or compounds where such combination is seen to be desirable or advantageous in achieving the desired effects of the methods described herein.

Various aspects of the present invention will be illustrated with reference to the following non-limiting examples.

EXAMPLE 1

Measurement of the dopamine receptor affinities for the R(+) and S(−) enantiomers of pramipexole.

The S(−) enantiomer of pramipexole has historically been characterized as a high affinity dopamine receptor ligand at the $D_2$ (both the S and L isoforms), $D_3$ and $D_4$ receptors, although the highest affinity is seen for the $D_3$ receptor subtype. The dopamine receptor ligand affinity of S(−) pramipexole from several clinical trials and journal publications has been tabulated (data is reproduced in Table 2). Although the conditions under which each study or experiment was carried out are slightly different, and different radio-ligands were used, the data show comparable affinities for the various dopamine receptors. Studies on the dopamine receptor affinity of the R(+) enantiomer of pramipexole are also shown in Table 2. These data demonstrate an unexpectedly large difference in the affinities of the two enantiomers of pramipexole for all dopamine receptors, with the R(+) enantiomer showing about 5,000-fold less affinity for the $D_3$ receptor subtype than the S(−) enantiomer, and a >10,000-fold lower affinity for the $D_{2L}$ and $D_{2S}$ receptor subtypes.

TABLE 2

Comparative human dopamine receptor affinity for pramipexole enantiomers

| Receptor | S(−) pramipexole * $K_i$(nM) | R(+) pramipexole ** $K_i$(nM) | R(+) pramipexole ** $Ic_{50}$ (nM) |
| --- | --- | --- | --- |
| $D_1$ | >50,000 | >100,000 | >100,000 |
| $D_{2S}$ | 2.2 | 29,000 | 87,000 |
| $D_{2L}$ | 3.9 | >100,000 | >100,000 |
| $D_3$ | 0.5 | 2,700 | 12,000 |
| $D_4$ | 5.1 | 8,700 | 22,000 |
| $D_5$ | >50,000 | >100,000 | >100,000 |

* Historic data
** Data from the present studies.

The R(+) pramipexole was supplied as dry powder to our contract research vendor Cerep by the manufacturer AMRI. Solutions of R(+) pramipexole were prepared from stock solutions in DMSO. Eight concentrations were tested: 50 nM, 100 nM, 500 nM, 1 µM, 5 µM, 10 µM, 50 µM, 100 µM. These concentrations were tested in either CHO (Chinese hamster ovary) or HEK293 (human embryonic kidney) cell lines expressing human cloned dopamine receptors ($D_1$, $D_{2S}$, $D_{2L}$, $D_3$, $D_4$, $D_5$). The radio-ligand in each case was either [$^3$H] spiperone or [$^3$H] SCH23390 (a classic $D_1$ dopamine receptor antagonist R-(+)-7-Chloro-8-hydroxy-3-methyl-1-phenyl-2,3,4,5-tetrahydro-1H-3-benzazepine hydrochloride), both antagonists at 0.3 nM. Incubation was for 60 minutes, and data were collected for 2 repeats using scintillation counting. Group results for the interaction of R(+) pramipexole with each receptor are expressed as both $IC_{50}$ and $K_i$ in Table 2.

These data indicate that $K_i$ values of pramipexole for these receptors are larger by a factor of at least 1000 for the R(+) enantiomer when compared to historic literature values for the S(−) enantiomer. These data also suggest that if dopamine receptor affinity is the major contributing factor to limiting dose tolerance of the S(−) enantiomer, then pure preparations of the R(+) enantiomer should have a maximum tolerated dose (MTD) and/or a no observable adverse effect level dose (NOAEL) of at least 1000 greater than the S(−) enantiomer's MTD and/or NOAEL. Thus, even a small contamination of the R(+) pramipexole compositions of the present invention by the S(−) enantiomer, at levels as low as 0.5% or less, may effect the observed MTD and NOEL.

EXAMPLE 2

In vivo studies to determine the MTD and NOAEL in dogs for 100% pure preparations of the R(+) and S(−) enantiomers of pramipexole, and a mixture (R 99.5%/S 0.5%)

The following in vivo study in beagle dogs was undertaken to test the hypothesis that the large observed difference in receptor binding affinities for the R(+) and S(−) enantiomers of pramipexole will translate to a large observed difference in the observed maximum tolerated dose (MTD) and/or no observable adverse effect level (NOAEL) of the two enantiomers. Dogs were administered preparations of each enantiomer prepared as a highly purified compound (100% pure preparations (within the limits of analytical detectability)), or a preparation of the R(+) enantiomer contaminated by 0.5% of the S(−) enantiomer of pramipexole.

Three groups of four non-naïve male beagle dogs were used in the study. Each group was administered various doses of either the R(+) or S(−) enantiomer prepared as a highly purified compound, or a preparation of the R(+) enantiomer contaminated by 0.5% of the S(−) enantiomer of pramipexole. Doses were administered orally by gavage and clinical observations were taken continuously following dosing: hourly for the first four hours, and then twice daily cage-side observations for the duration of the inter-dose or post-dose interval. Observations were made of clinical signs, mortality, injury and availability of food and water. Animals were fasted for 24 hr prior to dosing. Dogs in each group were exposed to only one drug, or the combination; each dose was administered only once, with a subsequent dose administered after a recovery period of 4 days. The data are summarized in Table 3.

A NOAEL was established at a dose level of 25 mg/kg for the R(+) enantiomer when administered to non-naive dogs, while a dose level of 75 mg/kg may be considered an MTD in non-naïve dogs. For the S(−) enantiomer, a NOAEL of 0.00125 mg/kg and an MTD of 0.0075 mg/kg was found. For the composition containing a mixture of the two enantiomers (99.5% R(+) pramipexole and 0.5% S(−) pramipexole), the NOAEL was found to be 0.25 mg/kg, which corresponds to a dose of 00125 mg/kg of the S(−) enantiomer, while the MTD is 1.5 mg/kg, which corresponds to a dose of 0.0075 mg/kg of the S(−) enantiomer. These data indicate that the NOAEL for the R(+) enantiomer of pramipexole is approximately 20,000-fold greater than for the S(−) enantiomer in non-naïve dogs, while the MTD is about 10,000-fold greater.

TABLE 3

Clinical observations in male beagle dogs for administration of pramipexole compositions
SUMMARY OF CLINCAL FINDINGS*

| | Dose Amount (mg/kg) | | | | | | | | |
|---|---|---|---|---|---|---|---|---|---|
| | 7.5 R(+) (Day 1) | 25 R(+) (Day 4) | 75 R(+) (Day 8) | 0.0075 S(−) (Day 1) | 0.025 S(−) (Day 4) | 0.00125 S(−) (Day 8) | 1.5 mixture** (Day 1) | 5 mixture (Day 4) | 0.25 mixture (Day 8) |
| Behavior/Activity | | | | | | | | | |
| Activity decreased | 0/4 | 0/4 | 2/4 | 3/4 | 4/4 | 0/4 | 4/4 | 4/4 | 0/4 |
| Convulsions - clonic | 0/4 | 0/4 | 1/4 | 0/4 | 0/4 | 0/4 | 0/4 | 0/4 | 0/4 |
| Salivation | 0/4 | 0/4 | 3/4 | 0/4 | 0/4 | 0/4 | 0/4 | 0/4 | 0/4 |
| Tremors | 0/4 | 0/4 | 4/4 | 1/4 | 3/4 | 0/4 | 1/4 | 2/4 | 0/4 |
| Excretion | | | | | | | | | |
| Emesis | 0/4 | 0/4 | 2/4 | 3/4 | 4/4 | 0/4 | 1/4 | 3/4 | 1/4 |
| Feces hard | 1/4 | 0/4 | 0/4 | 1/4 | 0/4 | 0/4 | 0/4 | 0/4 | 0/4 |
| Feces mucoid | 0/4 | 0/4 | 0/4 | 0/4 | 0/4 | 0/4 | 1/4 | 1/4 | 0/4 |
| Feces soft | 0/4 | 0/4 | 1/4 | 0/4 | 0/4 | 0/4 | 2/4 | 1/4 | 1/4 |
| Feces watery | 0/4 | 0/4 | 0/4 | 0/4 | 0/4 | 0/4 | 1/4 | 1/4 | 0/4 |
| External Appearance | | | | | | | | | |
| Lacrimation | 0/4 | 0/4 | 0/4 | 0/4 | 0/4 | 0/4 | 0/4 | 0/4 | 0/4 |
| Eye/Ocular | | | | | | | | | |
| Pupils dilated | 0/4 | 0/4 | 2/4 | 0/4 | 0/4 | 0/4 | 0/4 | 0/4 | 0/4 |
| Pelage/Skin | | | | | | | | | |
| Skin warm to touch | 1/4 | 0/4 | 1/4 | 0/4 | 0/4 | 0/4 | 0/4 | 0/4 | 0/4 |

*Number of animals affected/Total number of animals
**Mixture of 99.5% R(+) pramipexole and 0.5% S(−) pramipexole.

The data shown in Table 3 indicate that the receptor affinities identified (see Table 3) contribute in a straightforward fashion to the observed differences in the MTD and NOAEL doses for the R(+) and S(−) enantiomers of pramipexole. These data also indicate that the chiral purity for the R(+) enantiomer of pramipexole in embodiments of the compositions of the present invention (refer to Table 1) may need to be in excess of 99.9%, depending on the final total dose, to avoid the adverse side effects of S(−) pramipexole, while still achieving a therapeutically effective amount of the S(−) pramiepxole.

Further, the data in Table 3 demonstrate that the NOAEL and MTD for the combination composition (99.5% R(+) pramipexole and 0.5% S(−) pramipexole) may be determined directly by the dose of the S(−) enantiomer in the composition. Thus, a small (fractional percentage) contamination of a composition of R(+) pramipexole by the S(−) enantiomer may reduce the MTD and NOEL of the composition. For example, in these experiments, the MTD of pramipexole was reduced from 75 mg/kg for the R(+) enantiomer to a total dose of 1.5 mg/kg of the mixed composition (a factor of 50), and the NOAEL was reduced from 25 mg/kg to 0.25 mg/kg, respectively (a factor of 100). Since the shift in MTD and NOAEL may be predicted by the dose of the S(−) enantiomer of pramipexole in the mixture, the shift for any unknown mixture may be calculated based on the percentage contamination of the R(+) pramipexole by the S(−) enantiomer, relative to the MTD and NOAEL for S(−) pramipexole. This indicates that any contamination of an R(+) pramipexole dosing solution with S(−) pramipexole will have a measurable effect on these indicators of dose tolerability.

EXAMPLE 3

This example is a qualitative study on the dissolution of exemplary multicomponent capsules containing R(+) pramipexole and S(−) pramipexole.

Materials.

Drug Formulation. The drug formulation consisted of two capsules, an outer capsule filled with 100 mg of R(+) pramipexole and a smaller inner capsule filled with microcrystalline cellulose and 2 mg of S(−) pramipexole. Knopp provided AMRI with a 100 mg/mL solution of S(−) pramipexole in water that had been used to fill the inner capsule, blank inner and outer capsules to test the point of rupture, and exploratory combination capsules (100 mg R(+) pramipexole and 50 mg S(−) pramipexole) for the dissolution test. Normal phase, chiral HPLC was used for monitoring the release of R(+) pramipexole and S(−) pramipexole in simulated gastric fluid (SGF).

Concentration of the Inner Solution. The concentration of the 100 mg/mL S(−) pramipexole solution in water (lot # 084-126D) was verified by comparing the HPLC area response of the S(−) pramipexole peak to that of a known sample of S(−) pramipexole (AMRI lot # 06MRR122A). The concentration of S(−) pramipexole in 084-126D was calculated to be 99.03 mg/mL (99% of labeled concentration).

Dissolution Study. SGF (pH=1.2) was prepared by diluting 1 g of sodium chloride and 7 mL of concentrated HCl to 1 L with HPLC grade water. The dissolution experiment was run as follows: an exploratory combination capsule was placed in 10 mL of SGF and shaken under ambient conditions at 600 RPM for 60 minutes. Aliquots of 100 µL were pulled from the same sample vessel at various time points. The 100 µL samples of SGF solution were evaporated using a nitrogen bleed and heat and the residues were dissolved in the HPLC diluent and filtered through 0.45 µm syringe filters. Concentrations of the R(+) pramipexole and S(−) pramipexole enantiomers in the sample vessel were calculated by comparing the HPLC area response of each enantiomer to those of known standards. This experiment was performed in duplicate (experiment numbers SGF (1) (see Table 4) and SGF (2) (see Table 5)) and the results are also provided in average values (see Table 6). The tables and figures below summarize the results from these experiments.

TABLE 4

Experiment SGF (1)

| Time Point (minutes) | Concentration of R(+) pramipexole in SGF (1) Vessel (mg/mL) | Concentration of S(−) pramipexole in SGF (1) Vessel (mg/mL) |
|---|---|---|
| 3 | 0 | 0 |
| 4 | $1.824 \times 10^{-3}$ | 0 |
| 6 | $4.259 \times 10^{-2}$ | 0 |
| 8 | 6.441 | 0 |
| 10 | 8.443 | $6.978 \times 10^{-3}$ |
| 11 | 8.746 | $8.956 \times 10^{-3}$ |
| 12 | 8.767 | $1.083 \times 10^{-2}$ |
| 14 | 9.236 | $1.534 \times 10^{-3}$ |
| 15 | 9.510 | $1.769 \times 10^{-2}$ |
| 17 | 9.398 | $2.157 \times 10^{-2}$ |
| 18 | 9.127 | $2.223 \times 10^{-2}$ |
| 20 | 9.457 | $2.733 \times 10^{-2}$ |
| 25 | 9.579 | $3.764 \times 10^{-2}$ |
| 30 | 9.894 | $4.890 \times 10^{-2}$ |
| 60 | 9.530 | $5.197 \times 10^{-2}$ |
| 4320 | 3.624 | $9.367 \times 10^{-2}$ |

TABLE 5

Experiment SGF

| Time Point (minutes) | Concentration of R(+) pramipexole in SGF (2) Vessel (mg/mL) | Concentration of S(−) pramipexole in SGF (2) Vessel (mg/mL) |
|---|---|---|
| 3 | 0 | 0 |
| 4 | $2.245 \times 10^{-3}$ | 0 |
| 6 | $9.370 \times 10^{-2}$ | 0 |
| 8 | 8.250 | 0 |
| 10 | 8.787 | 0 |
| 11 | 9.131 | $5.803 \times 10^{-3}$ |
| 12 | 9.086 | $8.460 \times 10^{-3}$ |
| 14 | 9.092 | $1.466 \times 10^{-2}$ |
| 15 | 9.416 | $1.770 \times 10^{-2}$ |
| 17 | 9.477 | $2.196 \times 10^{-2}$ |
| 18 | 9.390 | $2.365 \times 10^{-2}$ |
| 20 | 9.493 | $2.867 \times 10^{-2}$ |
| 25 | 9.641 | $3.721 \times 10^{-2}$ |
| 30 | 9.406 | $4.242 \times 10^{-2}$ |
| 60 | 8.725 | $6.110 \times 10^{-2}$ |
| 4320 | 4.702 | $9.250 \times 10^{-2}$ |

TABLE 6

Average Values for Experiments SGF (1) and SGF (2)

| Time Point (minutes) | Average Concentrations of R(+) pramipexole (mg/mL) | Average Concentrations of S(−) pramipexole (mg/mL) |
|---|---|---|
| 3 | 0 | 0 |
| 4 | 0.002035 | 0 |
| 6 | 0.068145 | 0 |
| 8 | 7.345500 | 0 |
| 10 | 8.615000 | 0.003489 |
| 11 | 8.938500 | 0.007380 |
| 12 | 8.926500 | 0.009645 |

TABLE 6-continued

Average Values for Experiments SGF (1) and SGF (2)

| Time Point (minutes) | Average Concentrations of R(+) pramipexole (mg/mL) | Average Concentrations of S(−) pramipexole (mg/mL) |
|---|---|---|
| 14 | 9.164000 | 0.015000 |
| 15 | 9.463000 | 0.017695 |
| 17 | 9.437500 | 0.02176 |
| 18 | 9.258500 | 0.022940 |
| 20 | 9.475000 | 0.028000 |
| 25 | 9.610000 | 0.037425 |
| 30 | 9.650000 | 0.045660 |
| 60 | 9.127500 | 0.056535 |
| 4320 | 4.163000 | 0.093085 |

Discussion. These two experiments showed that there was a time difference between the release of R(+) pramipexole and the release of S(−) pramipexole from the exploratory combination capsules. Release of R(+) pramipexole was slow at first but quickly increased after 6 minutes. The concentration of R(+) pramipexole leveled off after 11 minutes. The release of S(−) pramipexole was slow and gradual and did not go to completion after one hour. This led to observed enantiomeric ratios of >100:1. A final 100 μL sample was taken from each vessel at approximately 72 hours (4320 min.). Both samples show a decrease in the R(+) pramipexole concentration and a slight increase in the S(−) pramipexole concentration. It is believed that the decrease in R(+) pramipexole concentration was due to light degradation, as the samples were inadvertently stored benchtop in a clear vial.

Although the present invention has been described in considerable detail with reference to certain preferred embodiments thereof, other versions are possible. Therefore the spirit and scope of the appended claims should not be limited to the description and the preferred versions contained within this specification.

What is claimed is:

1. A method of treating Parkinson's disease or the symptoms thereof comprising administering a solid unit dose of a therapeutically effective amount of R(+) pramipexole and an amount of S(−) pramipexole, wherein said therapeutically effective amount of R(+) pramipexole is from 100 milligrams to 3,000 milligrams and said amount of S(−) pramipexole is from 1.5 milligrams to 4.5 milligrams.

2. The method of claim 1, wherein said therapeutically effective amount of R(+) pramipexole is from 300 milligrams to 1,500 milligrams.

3. The method of claim 1, wherein said therapeutically effective amount of R(+) pramipexole is from 500 milligrams to 1,000 milligrams.

4. The method of claim 1, wherein said solid unit dose of a therapeutically effective amount of R(+) pramipexole and an amount of S(−) pramipexole is administered from one to five times a day.

5. The method of claim 1, wherein said solid unit dose of a therapeutically effective amount of R(+) pramipexole and an amount of S(−) pramipexole is administered three times a day.

6. The method of claim 1, wherein said solid unit dose of a therapeutically effective amount of R(+) pramipexole and an amount of S(−) pramipexole is a single pharmaceutical composition.

7. The method of claim 1, wherein said solid unit dose of a therapeutically effective amount of R(+) pramipexole and an amount of S(−) pramipexole is more than one pharmaceutical composition.

8. The method of claim 1, wherein said solid unit dose of a therapeutically effective amount of R(+) pramipexole and an amount of S(−) pramipexole is administered once a day.

9. The method of claim 1, wherein said solid unit dose of a therapeutically effective amount of R(+) pramipexole and an amount of S(−) pramipexole is administered two times a day.

10. The method of claim 1, wherein said solid unit dose is selected from a tablet, a capsule, a lozenge, a pellet, a granule, a bead, a cachet, an implant, a suppository, a pessary, and a powder.

11. The method of claim 1, wherein said solid unit dose is a pharmaceutical composition selected from an immediate release pharmaceutical composition and a sustained release pharmaceutical composition.

12. A method of treating Parkinson's disease or the symptoms thereof comprising orally administering a unit dose of a therapeutically effective amount of R(+) pramipexole and an amount of S(−) pramipexole, wherein said therapeutically effective amount of R(+) pramipexole is from 100 milligrams to 3,000 milligrams and said amount of S(−) pramipexole is from 1.5 milligrams to 4.5 milligrams.

13. The method of claim 12, wherein said therapeutically effective amount of R(+) pramipexole is from 300 milligrams to 1,500 milligrams.

14. The method of claim 12, wherein said therapeutically effective amount of R(+) pramipexole is from 500 milligrams to 1,000 milligrams.

15. The method of claim 12, wherein said unit dose of a therapeutically effective amount of R(+) pramipexole and an amount of S(−) pramipexole is administered from one to five times a day.

16. The method of claim 12, wherein said unit dose of a therapeutically effective amount of R(+) pramipexole and an amount of S(−) pramipexole is administered three times a day.

17. The method of claim 12, wherein said unit dose of a therapeutically effective amount of R(+) pramipexole and an amount of S(−) pramipexole is a single pharmaceutical composition.

18. The method of claim 12, wherein said unit dose of a therapeutically effective amount of R(+) pramipexole and an amount of S(−) pramipexole is more than one pharmaceutical composition.

19. The method of claim 12, wherein said unit dose of a therapeutically effective amount of R(+) pramipexole and an amount of S(−) pramipexole is administered once a day.

20. The method of claim 12, wherein said unit dose of a therapeutically effective amount of R(+) pramipexole and an amount of S(−) pramipexole is administered two times a day.

21. The method of claim 12, wherein said unit dose is selected from a tablet, a capsule, a lozenge, a pellet, a granule, a bead, a cachet, a powder, and a liquid.

22. The method of claim 12, wherein said unit dose is a pharmaceutical composition selected from an immediate release pharmaceutical composition and a sustained release pharmaceutical composition.

23. A method of treating Parkinson's disease or the symptoms thereof comprising administering a solid unit dose of a therapeutically effective amount of R(+) pramipexole and an amount of S(−) pramipexole, wherein said therapeutically effective amount of R(+) pramipexole is from 100 milligrams to 3,000 milligrams and said amount of S(−) pramipexole is 4.5 milligrams.

24. The method of claim 23, wherein said therapeutically effective amount of R(+) pramipexole is from 300 milligrams to 1,500 milligrams.

25. The method of claim 23, wherein said therapeutically effective amount of R(+) pramipexole is from 500 milligrams to 1,000 milligrams.

26. The method of claim 23, wherein said solid unit dose of a therapeutically effective amount of R(+) pramipexole and an amount of S(−) pramipexole is a single pharmaceutical composition.

27. The method of claim 23, wherein said solid unit dose of a therapeutically effective amount of R(+) pramipexole and an amount of S(−) pramipexole is more than one pharmaceutical composition.

28. The method of claim 23, wherein said solid unit dose of a therapeutically effective amount of R(+) pramipexole and an amount of S(−) pramipexole is administered once a day.

29. The method of claim 23, wherein said solid unit dose is selected from a tablet, a capsule, a lozenge, a pellet, a granule, a bead, a cachet, an implant, a suppository, a pessary, and a powder.

30. The method of claim 23, wherein said solid unit dose is a pharmaceutical composition selected from an immediate release pharmaceutical composition and a sustained release pharmaceutical composition.

31. A method of treating Parkinson's disease or the symptoms thereof comprising orally administering a unit dose of a therapeutically effective amount of R(+) pramipexole and an amount of S(−) pramipexole, wherein said therapeutically effective amount of R(+) pramipexole is from 100 milligrams to 3,000 milligrams and said amount of S(−) pramipexole is 4.5 milligrams.

32. The method of claim 31, wherein said therapeutically effective amount of R(+) pramipexole is from 300 milligrams to 1,500 milligrams.

33. The method of claim 31, wherein said therapeutically effective amount of R(+) pramipexole is from 500 milligrams to 1,000 milligrams.

34. The method of claim 31, wherein said unit dose of a therapeutically effective amount of R(+) pramipexole and an amount of S(−) pramipexole is a single pharmaceutical composition.

35. The method of claim 31, wherein said unit dose of a therapeutically effective amount of R(+) pramipexole and an amount of S(−) pramipexole is more than one pharmaceutical composition.

36. The method of claim 31, wherein said unit dose of a therapeutically effective amount of R(+) pramipexole and an amount of S(−) pramipexole is administered once a day.

37. The method of claim 31, wherein said unit dose is selected from a tablet, a capsule, a lozenge, a pellet, a granule, a bead, a cachet, a powder, and a liquid.

38. The method of claim 31, wherein said unit dose is a pharmaceutical composition selected from an immediate release pharmaceutical composition and a sustained release pharmaceutical composition.

39. The method of claim 1, wherein said solid unit dose is administered in a route selected from orally, topically, sublingually, bucally, intravaginally, and rectally.

40. The method of claim 23, wherein said solid unit dose is administered in a route selected from orally, topically, sublingually bucally, intravaginally, and rectally.

41. The method of claim 1, wherein said amount of S(−) pramipexole is 1.5 milligrams.

42. The method of claim 12, wherein said amount of S(−) pramipexole is 1.5 milligrams.

* * * * *